(12) United States Patent
Unagami et al.

(10) Patent No.: US 9,832,821 B2
(45) Date of Patent: Nov. 28, 2017

(54) METHOD FOR CONTROLLING INFORMATION TERMINAL APPARATUS

(71) Applicant: Panasonic Intellectual Property Corporation of America, Torrance, CA (US)

(72) Inventors: Yuji Unagami, Osaka (JP); Motoji Ohmori, Osaka (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 283 days.

(21) Appl. No.: 14/470,643

(22) Filed: Aug. 27, 2014

(65) Prior Publication Data

US 2015/0074237 A1    Mar. 12, 2015

(30) Foreign Application Priority Data

Sep. 9, 2013 (JP) ................ 2013-186054

(51) Int. Cl.
| | |
|---|---|
| G06F 15/16 | (2006.01) |
| H05B 6/64 | (2006.01) |
| G06Q 99/00 | (2006.01) |
| H05B 6/66 | (2006.01) |
| G06F 17/30 | (2006.01) |

(52) U.S. Cl.
CPC .......... *H05B 6/6435* (2013.01); *G06Q 99/00* (2013.01); *H05B 6/668* (2013.01); *G06F 15/16* (2013.01); *G06F 17/30* (2013.01)

(58) Field of Classification Search
None
See application file for complete search history.

(56) References Cited

U.S. PATENT DOCUMENTS

| | | | | |
|---|---|---|---|---|
| 6,949,729 B1 * | 9/2005 | Ishikawa | ............... | H05B 6/688 219/702 |
| 8,639,214 B1 * | 1/2014 | Fujisaki | ............... | H04M 11/007 379/88.03 |

(Continued)

FOREIGN PATENT DOCUMENTS

| | | |
|---|---|---|
| JP | 2000-346367 | 12/2000 |
| JP | 2002-288358 | 10/2002 |

*Primary Examiner* — Viet Vu
*Assistant Examiner* — James Edwards
(74) *Attorney, Agent, or Firm* — Greenblum & Bernstein, P.L.C.

(57) ABSTRACT

A control method causes a computer of an information terminal apparatus to perform a process including: receiving, from a first server, first display data causing a user of the information terminal apparatus to confirm the purpose of use of recipe information and asking for the permission to collect the recipe information; accessing a second server and receiving selected recipe information and control data for a cooker for preparation based on the selected recipe information; and when it is selected to permit collecting the recipe information for a purpose of use related to health care, and it is determined that selected recipe information corresponding to the set control data has an identifier indicating that the recipe is for food related to a specific constitution, disorder, disease, or allergy, transmitting the selected recipe information with the identifier, in association with a user ID of the information terminal apparatus, to the first server.

16 Claims, 27 Drawing Sheets

(56) References Cited

U.S. PATENT DOCUMENTS

| | | | | |
|---|---|---|---|---|
| 2003/0187682 A1* | 10/2003 | Ozawa | ............... | H05B 6/688 |
| | | | | 705/1.1 |
| 2008/0235232 A1* | 9/2008 | Moses | ............... | G06Q 10/10 |
| 2009/0070234 A1* | 3/2009 | Peters | ............... | B67D 1/0041 |
| | | | | 705/26.1 |
| 2009/0144081 A1* | 6/2009 | Harlan | ............... | G06Q 50/22 |
| | | | | 705/2 |
| 2010/0057540 A1* | 3/2010 | Tanaka | ............... | G06Q 10/087 |
| | | | | 705/15 |
| 2010/0332493 A1* | 12/2010 | Haas | ............... | G06F 17/3064 |
| | | | | 707/759 |
| 2012/0284333 A1* | 11/2012 | Neff | ............... | G06F 17/30528 |
| | | | | 709/204 |
| 2013/0052616 A1* | 2/2013 | Silverstein | ............... | G09B 19/00 |
| | | | | 434/127 |
| 2013/0214935 A1* | 8/2013 | Kim | ............... | G08C 17/02 |
| | | | | 340/870.02 |
| 2014/0101233 A1* | 4/2014 | Mina | ............... | H04L 29/06047 |
| | | | | 709/203 |
| 2014/0272817 A1* | 9/2014 | Park | ............... | G09B 5/02 |
| | | | | 434/127 |

\* cited by examiner

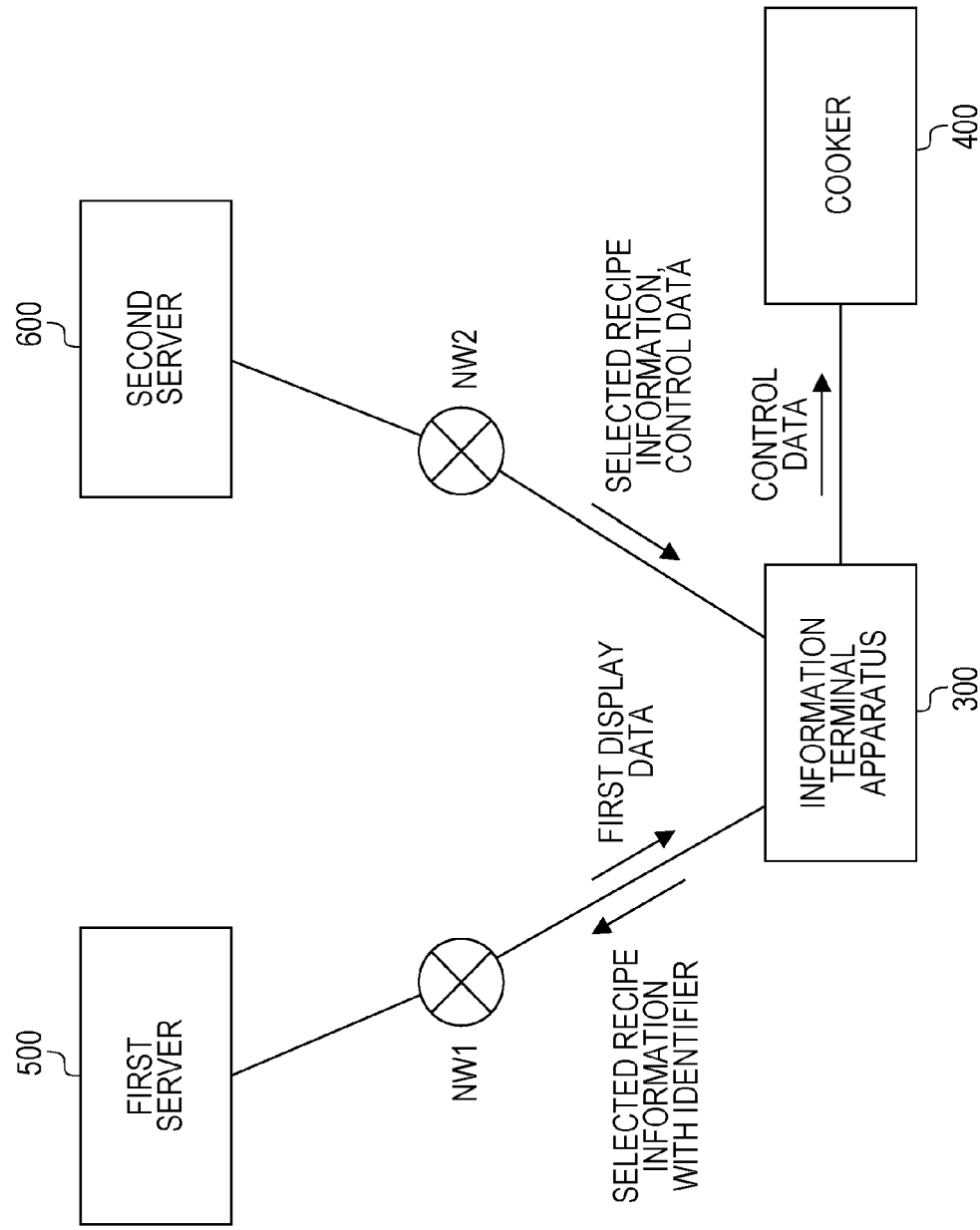

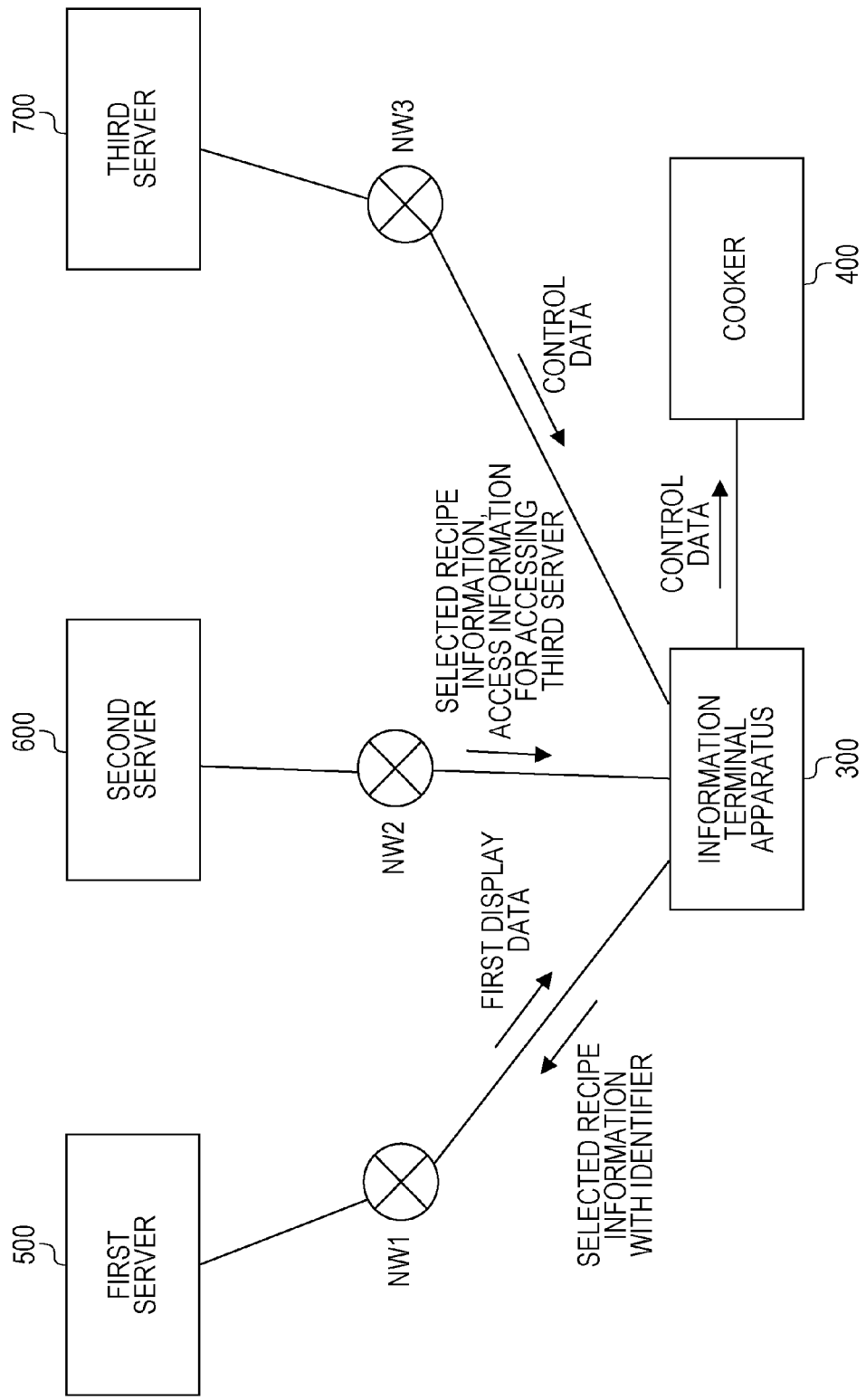

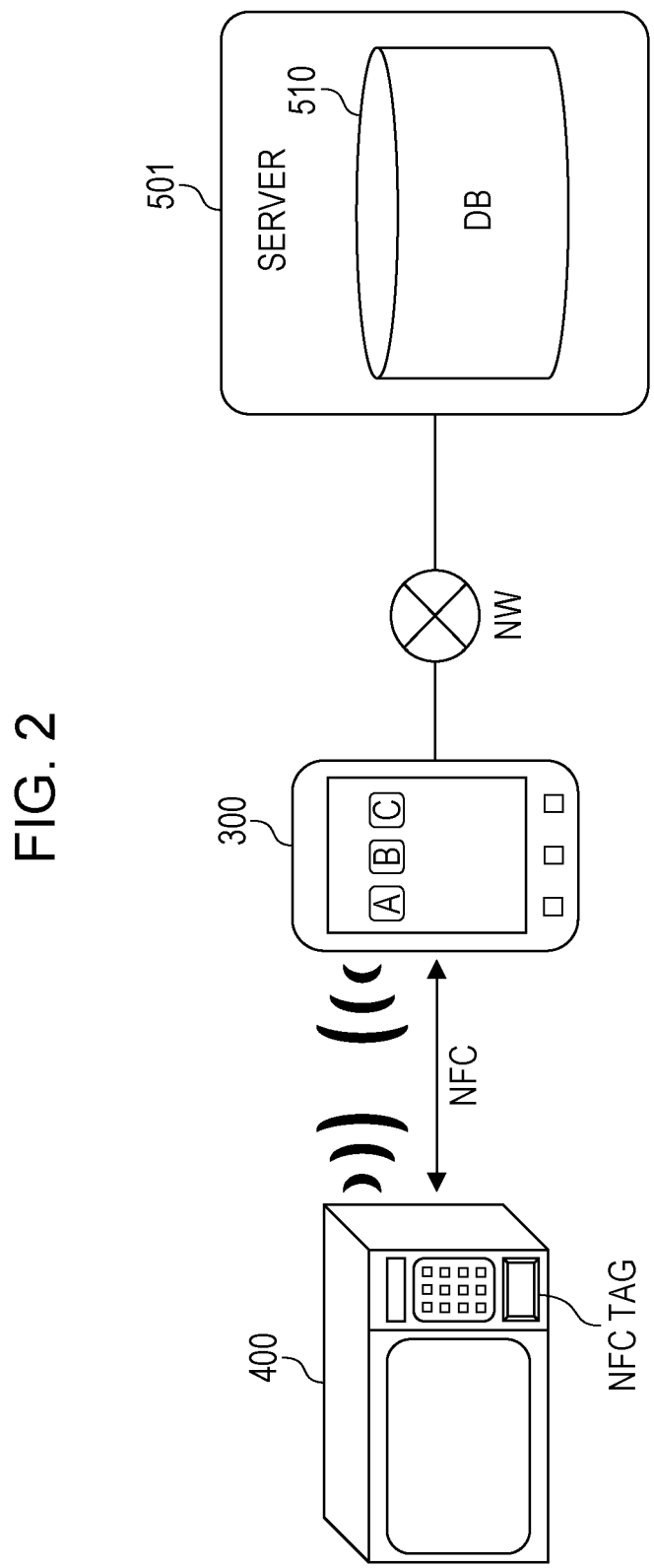

FIG. 7

| USER ID | PERSONAL INFORMATION |
|---|---|
| 001 | NAME: TARO MATSUSHITA<br>ADDRESS: 1-19 MINATO-KU TOKYO<br>DATE OF BIRTH: MARCH 3, 1990<br>SEX: MALE<br>EMAIL ADDRESS: sato@aaa.com<br>HOBBY: READING |
| 002 | NAME: HANAKO SUZUKI<br>ADDRESS: 3-10 FUKUSHIMA-KU OSAKA<br>DATE OF BIRTH: OCTOBER 5, 1980<br>SEX: FEMALE<br>EMAIL ADDRESS: yamada@aaa.com<br>HOBBY: AEROBICS |
| ... | ... |

FIG. 9

[PROVISION OF RECIPE INFORMATION]

WOULD YOU ALLOW RECIPE INFORMATION THAT YOU HAVE SELECTED TO BE SENT IN ORDER FOR US TO COLLECT AND UTILIZE ALLERGY-RELATED INFORMATION?
* PLEASE SELECT "YES" OR "NO".

◉ YES    ◉ NO

PLEASE SELECT A PERIOD IN WHICH RECIPE INFORMATION THAT YOU HAVE SELECTED IS TO BE SENT TO US.

◉ 30 DAYS
○ 180 DAYS
○ UNLIMITED

SEND

FIG. 10

| USER ID | NAME | WHETHER OR NOT COLLECTION IS PERMITTED |
|---|---|---|
| 001 | TARO MATSUSHITA | HEALTH CARE PURPOSE<br>ALLERGY-RELATED: PERMITTED, 180 DAYS<br>WEIGHT-CONTROL-RELATED: PERMITTED, 180 DAYS<br>SPECIFIC-DISEASE-RELATED: PERMITTED, 180 DAYS<br>ADVERTISEMENT PURPOSE<br>PROVISION OF NEW RECIPE INFORMATION: FORBIDDEN<br>PROVISION OF NEW PRODUCT INFORMATION: FORBIDDEN<br>... |
| 002 | HANAKO SUZUKI | HEALTH CARE PURPOSE<br>ALLERGY-RELATED: PERMITTED, UNLIMITED<br>WEIGHT-CONTROL-RELATED: PERMITTED, UNLIMITED<br>SPECIFIC-DISEASE-RELATED: PERMITTED, UNLIMITED<br>ADVERTISEMENT PURPOSE<br>PROVISION OF NEW RECIPE INFORMATION: PERMITTED, UNLIMITED<br>PROVISION OF NEW PRODUCT INFORMATION: PERMITTED, UNLIMITED<br>... |
| ... | ... | |

FIG. 11

[DISEASE-RELATED]
MAY WE COLLECT AND UTILIZE ALLERGY-RELATED INFORMATION AND SEND YOU AN AD?
* PLEASE SELECT "YES" OR "NO".

○ YES    ◉ NO

FOR THOSE WHO HAVE PROVIDED US WITH INFORMATION, WE ARE PLEASED TO FURTHER OFFER VARIOUS SERVICES. IF YOU ARE INTERESTED, PLEASE CLICK THE "NEXT" BUTTON.

NEXT

FIG. 13

| RECIPE ID | NAME OF FOOD ITEM | INGREDIENTS | IDENTIFIER | CONTROL DATA |
|---|---|---|---|---|
| RE001 | HAMBURG STEAK | GROUND MEAT<br>ONIONS<br>MILK<br>BREAD CRUMBS<br>SALT AND PEPPER | EGG ALLERGY | TWELVE MINUTES, OVEN 230 DEGREES<br>TEN MINUTES, OVEN 230 DEGREES |
| RE002 | JAPANESE STEAMED EGG CUSTARD | SOYMILK<br>BITTERN<br>CHICKEN<br>DRIED MUSHROOMS<br>GINGKO NUTS<br>FISH CAKE | EGG ALLERGY<br>LOW CALORIES<br>DIABETES | FOUR MINUTES, 500 W |
| ... | ... | ... | ... | ... |
| RW001 | PANCAKES | RICE FLOUR<br>WATER<br>TOFU<br>MILK | WHEAT ALLERGY | THREE MINUTES, 500 W |
| ... | ... | ... | ... | ... |
| ... | ... | ... | ... | ... |

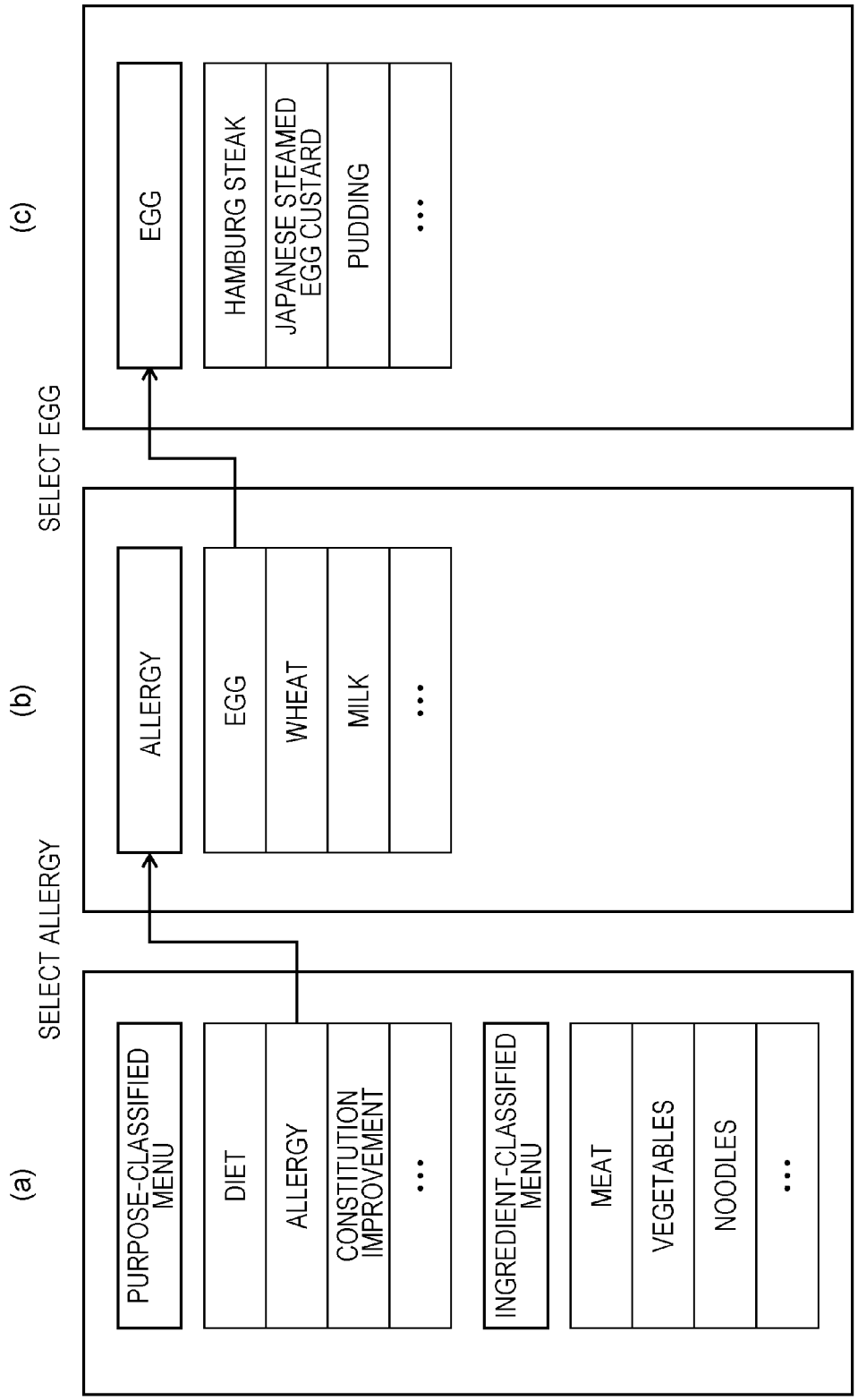

FIG. 19

| USER ID | NAME | TAG | RECIPE ID | DATE |
|---|---|---|---|---|
| 001 | TARO MATSUSHITA | EGG | RE002 | JANUARY 10, 2013 |
| | | ... | ... | ... |
| 002 | HANAKO SUZUKI | WHEAT | RW001 | FEBRUARY 1, 2013 |
| | | ... | ... | ... |
| ... | | ... | ... | ... |

FIG. 20

[ALLERGY-RELATED] (CONFIRMATION SCREEN)
WOULD YOU ALLOW UTILIZATION OF HISTORY INFORMATION COLLECTED FROM THE FOLLOWING HOME APPLIANCES IN ORDER FOR US TO COLLECT AND UTILIZE ALLERGY-RELATED INFORMATION?

AIR PURIFIER

- OPERATION FREQUENCY INFORMATION  ☑ YES, I WOULD PROVIDE THE INFORMATION.  ☐ NO, I WOULD NOT PROVIDE THE INFORMATION.
- INFORMATION RELATED TO FREQUENCY OF USING ALLERGEN-INHIBITORY MODE  ☑ YES, I WOULD PROVIDE THE INFORMATION.  ☐ NO, I WOULD NOT PROVIDE THE INFORMATION.

COOKING HOME APPLIANCE (MICROWAVE OVEN)

- INFORMATION OF USED COOKING MODE(S)  ☑ YES, I WOULD PROVIDE THE INFORMATION.  ☐ NO, I WOULD NOT PROVIDE THE INFORMATION.
- INFORMATION OF USED FOOD MATERIAL(S)  ☐ YES, I WOULD PROVIDE THE INFORMATION.  ☑ NO, I WOULD NOT PROVIDE THE INFORMATION.

[ SEND ]

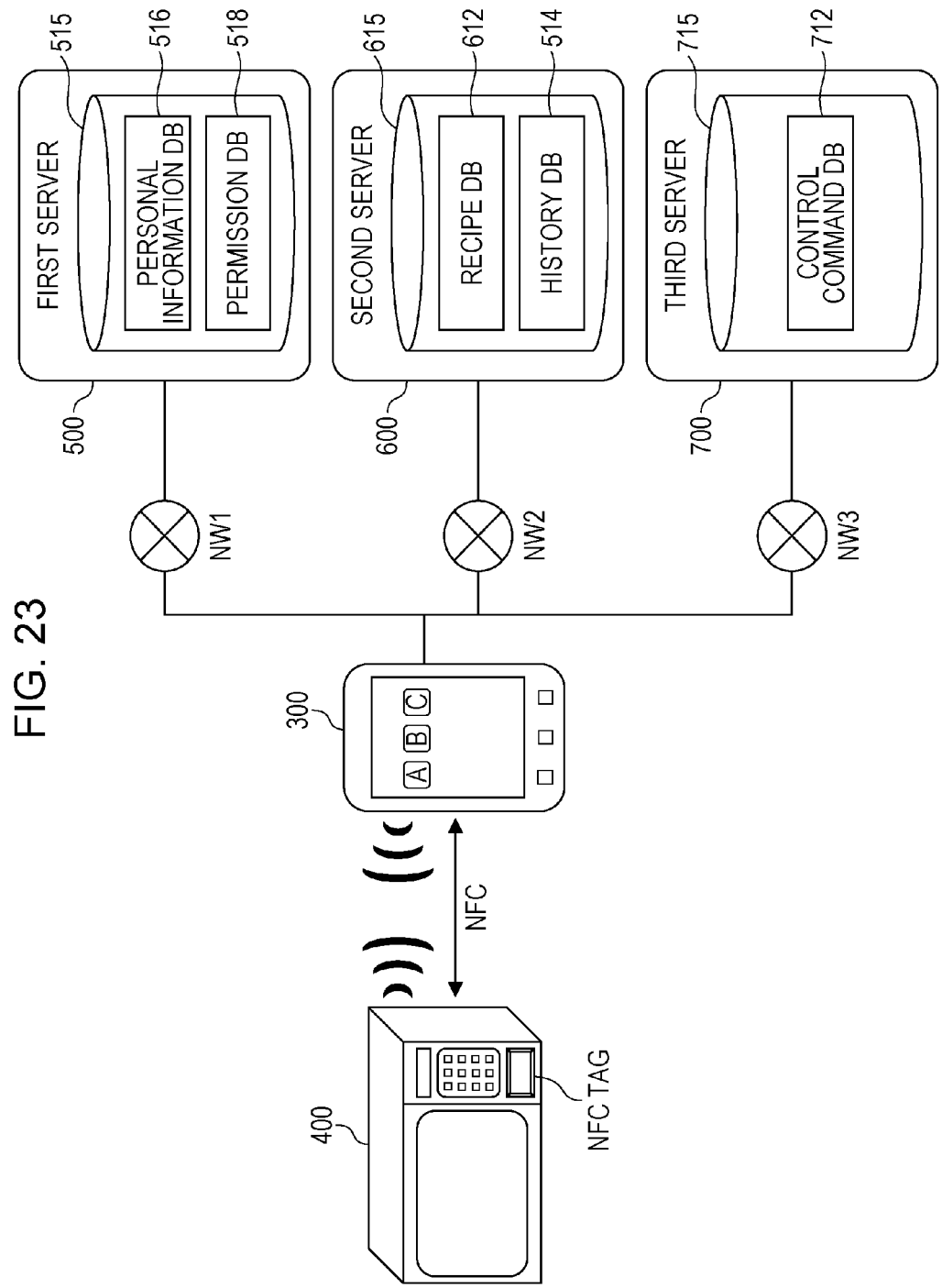

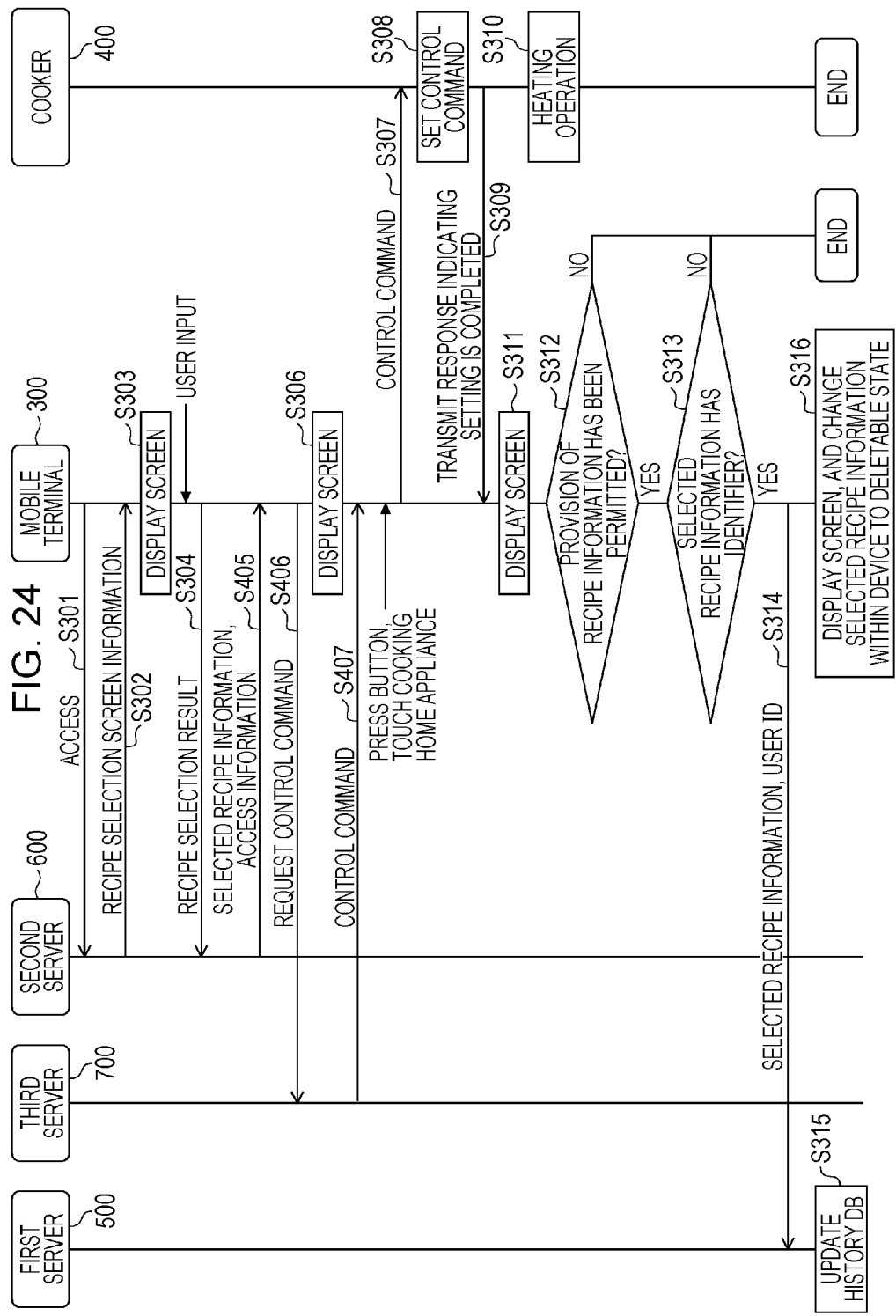

METHOD FOR CONTROLLING INFORMATION TERMINAL APPARATUS

CROSS REFERENCES TO RELATED APPLICATIONS

This Application claims priority to Japanese Patent Application No. 2013-186054, filed on Sep. 9, 2013, the contents of which are hereby incorporated by reference.

BACKGROUND

1. Technical Field

The present disclosure relates to a method for controlling an information terminal apparatus that obtains recipe information for a food item from a server device via a network.

2. Description of the Related Art

Japanese Patent No. 4342117 discloses a food recipe information providing system that transmits recipe information for a food item to a user terminal. In this food recipe information providing system, a host server transmits food recipe information for a first food item to the user terminal in response to a request signal transmitted from the user terminal, and transmits to the user terminal food recipe information for a second food item that can be prepared while a cooker prepares the first food item in accordance with the food recipe information. Accordingly, the user can easily find a second food item that can be prepared while a first food item is being prepared.

Japanese Patent No. 4188524 discloses a microwave oven system. In this microwave oven system, a host computer stores homepage information including a menu-to-prepare selection screen for selecting a desired food item from among a plurality of food items. An information processing apparatus obtains the homepage information from the host computer, and displays a homepage screen based on the obtained homepage information. A microwave oven displays, on a displaying unit, display data included in supplied information supplied from the information processing apparatus, recognizes heating control data included in the supplied information in response to a user operation, and performs a heating operation.

The homepage information transmitted from the host computer to the information processing apparatus includes food data and screen data. The food data includes, for each of a plurality of food items, description display information for describing how to prepare the food item, which includes the name of the food item, ingredients, and information on a cooker(s) to use, and heating control data for heating the food item transferred to the microwave oven. The screen data includes information for displaying a food item selected on the menu-to-prepare selection screen, and display information of a transfer instruction button operated for transferring food data to the information processing apparatus. Data supplied as supplied information from the information processing apparatus to the microwave oven includes the above-mentioned heating control data and display data based on the above-mentioned description display information.

Besides the above-described related art, a service model referred to as a "cloud service" has been investigated in recent years. As part of this investigation, it has been investigated to accumulate, from a home appliance, information regarding the use of the home appliance by a user in a server that provides a cloud service, and provide a service that suits the user by utilizing the accumulated information.

SUMMARY

However, the above-mentioned cloud service is currently under investigation, and further investigation and improvement are necessary for realization. In particular, there has not been a cloud system that collects and utilizes recipe information selected by a user, which has been specifically investigated in terms of the protection of the user's privacy. Thus, a non-limiting exemplary embodiment of the present disclosure provides a method for controlling an information processing terminal that realizes a cloud system that collects and utilizes recipe information selected by a user.

A method for controlling an information terminal apparatus, according to an embodiment of the present disclosure, is a method for controlling an information terminal apparatus connectable to a first server that collects information and to a second server that provides recipe information indicating a cooking recipe used in a cooker. The method causes a computer of the information terminal apparatus to perform a process including: (1) receiving, from the first server via a first network, first display data for causing a user of the information terminal apparatus to confirm a purpose of use of the recipe information and for asking the user for a permission to collect the recipe information; (2) displaying the first display data on a display of the information terminal apparatus; (3) accessing the second server via a second network and receiving, from the second server, selected recipe information selected from among a plurality of items of recipe information on the information terminal apparatus and control data for the cooker for a preparation based on the selected recipe information, the plurality of items of recipe information including recipe information with an identifier indicating that the recipe information is for a food item related to a specific constitution, disorder, disease, or allergy; (4) displaying the selected recipe information on the display of the information terminal apparatus; (5) setting the control data in the cooker by using the control data; and (6) in a case where it has been selected to permit collecting the recipe information for a purpose of use related to health care, out of the purpose of use on the information terminal apparatus using the first display data, and in a case where it has been determined that selected recipe information corresponding to the set control data has the identifier, transmitting the selected recipe information with the identifier, in association with a user ID of the information terminal apparatus, to the first server.

These general and specific aspects may be implemented using a system, a method, and a computer program, and any combination of systems, methods, and computer programs.

According to the above-described embodiment, further improvement can be made for realization of a cloud service that collects and utilizes recipe information selected by a user. Additional benefits and advantages of the disclosed embodiments will be apparent from the specification and Figures. The benefits and/or advantages may be individually provided by the various embodiments and features of the specification and Figures, and need not all be provided in order to obtain one or more of the same.

BRIEF DESCRIPTION OF THE DRAWINGS

FIG. 1A is a diagram illustrating an overview of the configuration of a cooker system according to an embodiment of the present disclosure;

FIG. 1B is a diagram illustrating an overview of the configuration of a cooker system according to another embodiment of the present disclosure;

FIG. 2 is a diagram schematically illustrating the configuration of a cooker system according to a first embodiment of the present disclosure;

FIG. 7 is a diagram illustrating an example of personal information accumulated in a personal information database (DB);

FIG. 9 is a diagram illustrating an example of a purpose-of-provision confirmation screen;

FIG. 10 is a diagram illustrating an example of information stored in a permission DB;

FIG. 11 is a diagram illustrating another example of the purpose-of-provision confirmation screen;

FIG. 13 is a diagram illustrating an example of information stored in a recipe DB;

FIG. 14 is a diagram illustrating an example of a recipe selection screen;

FIG. 19 is a diagram illustrating an example of information recorded in a history DB;

FIG. 20 is a diagram illustrating another exemplary screen for setting whether or not collecting information is permitted;

FIG. 23 is a diagram illustrating the configuration of an embodiment of a cooker system including three servers;

FIG. 24 is a flowchart illustrating a recipe information obtaining and transmitting process according to the embodiment illustrated in FIG. 23;

DETAILED DESCRIPTION

Figure 3:
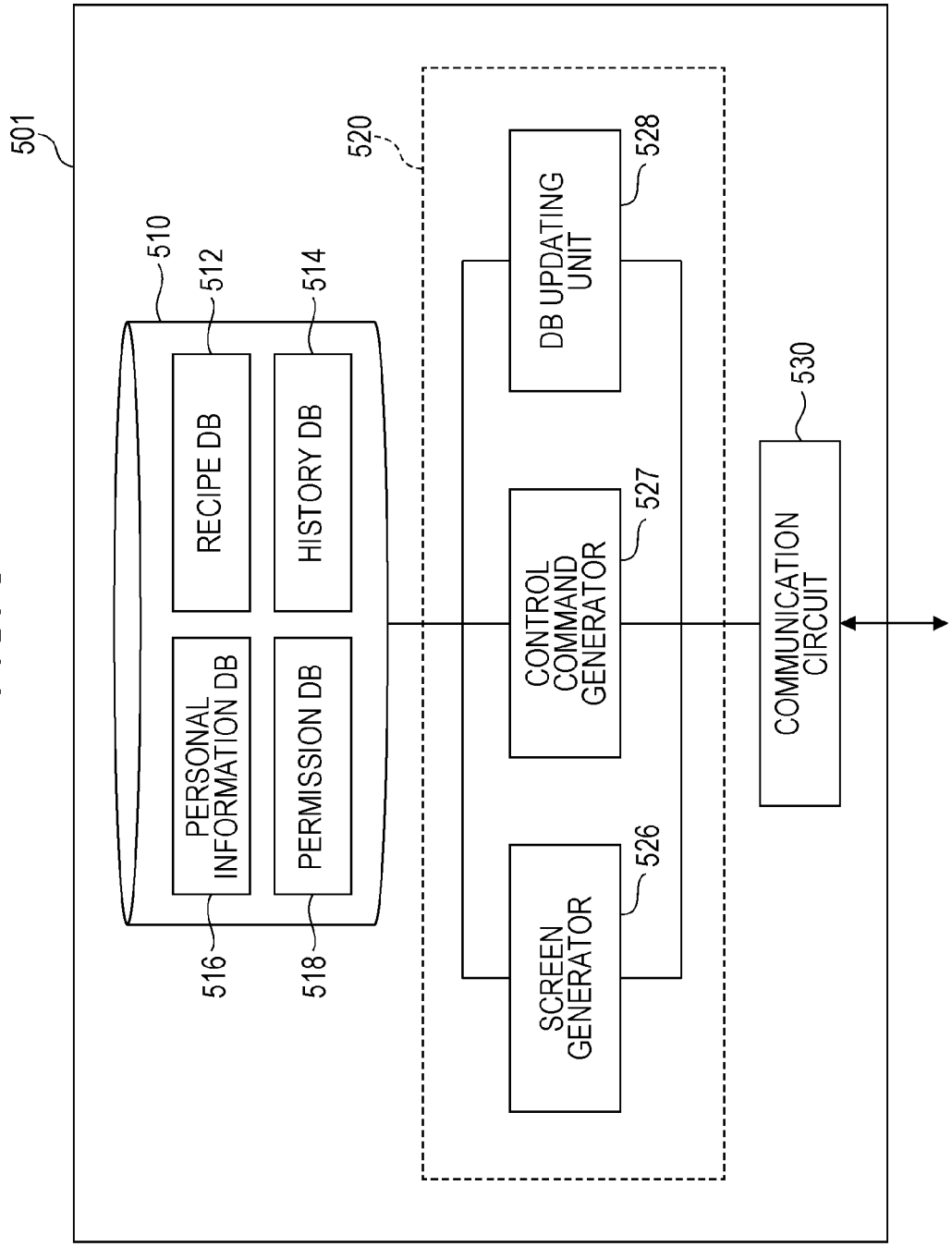
FIG. 3 is a block diagram illustrating the configuration of a server.

1. Findings that Form Basis of the Present Disclosure

Before description of a specific embodiment, findings that form the basis of the present disclosure will be described.

In the food recipe information providing system disclosed in Japanese Patent No. 4342117, the host server transmits food recipe information to the user terminal. However, the food recipe information remains to be used by the user of the terminal which has received the information, and no investigations have been conducted to apply the recipe information to a cloud service.

In Japanese Patent No. 4188524, the information processing apparatus displays a homepage screen on the basis of homepage information held by the host computer, and transmits supplied information to the microwave oven. As mentioned above, the supplied information includes heating control data for heating the food item, and display data based on description display information for describing how to prepare the food item, which includes the name of the food item, ingredients, and information of a cooker(s) to use. The microwave oven displays a screen based on the display data, recognizes the heating control data, and performs a heating operation. That is, the microwave oven obtains and displays information corresponding to description display information included in homepage information held by the host computer via the information processing apparatus, and performs a heating operation based on the heating control data. However, the description display information and the heating control data remain to be used by a user of the microwave oven, and no investigations have been conducted to apply these items of information to a cloud service.

The inventors of the present disclosure have conducted the following investigations for providing a cloud service using information (use information) regarding the use of a home appliance. In particular, when collecting use information, it is necessary to ask the user of a home appliance for the permission to collect use information. There has not been a system that specifically investigates this point yet.

For users, it is desirable that use information be provided to a minimum range. That is, it is desirable to reduce the risk of leakage of personal information as a result of providing use information to an unnecessarily wide range. In contrast, it is bothersome to ask the user for the permission to provide use information every time use information is to be provided.

Conversely, for a service provider who receives provision of use information, it is desirable to ask for provision of use information in units corresponding to applications of service provision. If provision of use information in units that are smaller than units corresponding to applications of service provision is received, information becomes overemphasized, resulting in an obstacle to appropriate service provision.

The inventors have conducted the following investigations for improvement in view of these points.

2. Brief Overview of the Present Disclosure

A method of controlling an information terminal apparatus according to an embodiment of the present disclosure is a method for controlling an information terminal apparatus connectable to a first server that collects information and to a second server that provides recipe information indicating a cooking recipe used in a cooker. The method causes a computer of the information terminal apparatus to perform a process including: (1) receiving, from the first server via a first network, first display data for causing a user of the information terminal apparatus to confirm a purpose of use of the recipe information and for asking the user for a permission to collect the recipe information; (2) displaying the first display data on a display of the information terminal apparatus; (3) accessing the second server via a second network and receiving, from the second server, selected recipe information selected from among a plurality of items of recipe information on the information terminal apparatus and control data for the cooker for a preparation based on the selected recipe information, the plurality of items of recipe information including recipe information with an identifier indicating that the recipe information is for a food item related to a specific constitution, disorder, disease, or allergy; (4) displaying the selected recipe information on the display of the information terminal apparatus; (5) setting the control data in the cooker by using the control data; and (6) in a case where it has been selected to permit collecting the recipe information for a purpose of use related to health care, out of the purpose of use on the information terminal apparatus using the first display data, and in a case where it has been determined that selected recipe information corresponding to the set control data has the identifier, transmitting the selected recipe information with the identifier, in association with a user ID of the information terminal apparatus, to the first server.

In a case where it has been determined that selected recipe information corresponding to the control data does not have the identifier, the selected recipe information, which does not have the identifier, may not be transmitted to the first server.

The first server may be a server that is identical to the second server.

The first server may be a server that is different from the second server.

The process may further include, when setting the control data in the cooker by using the control data, determining whether or not selected recipe information corresponding to the control data has the identifier.

The process may further include, in a case of setting the control data in the cooker by using the control data, after receiving a response from the cooker indicating that the setting is completed, transmitting the selected recipe information to the first server.

The process may further include, after transmitting the selected recipe information with the identifier to the first server, causing the selected recipe information to be in a state in which the selected recipe information is deletable from a memory of the information terminal apparatus.

The process may further include, after transmitting the selected recipe information with the identifier to the first server, displaying, on the display of the information terminal apparatus, second display data indicating that the selected recipe information has been transmitted to the first server.

The first display data may include an item for specifying a period in which the recipe information is provided.

The cooker may be a microwave oven.

A computer program according to another embodiment of the present disclosure is used in an information terminal apparatus connectable to a first server that collects information and to a second server that provides recipe information indicating a cooking recipe used in a cooker. The program causes a computer of the information terminal apparatus to perform a process including: (1) receiving, from the first server via a first network, first display data for causing a user of the information terminal apparatus to confirm a purpose of use of the recipe information and for asking the user for a permission to collect the recipe information; (2) displaying the first display data on a display of the information terminal apparatus; (3) accessing the second server via a second network and receiving, from the second server, selected recipe information selected from among a plurality of items of recipe information on the information terminal apparatus and control data for the cooker for a preparation based on the selected recipe information, the plurality of items of recipe information including recipe information with an identifier indicating that the recipe information is for a food item related to a specific constitution, disorder, disease, or allergy; (4) displaying the selected recipe information on the display of the information terminal apparatus; (5) setting the control data in the cooker by using the control data; and (6) in a case where it has been selected to permit collecting the recipe information for a purpose of use related to health care, out of the purpose of use on the information terminal apparatus using the first display data, and in a case where it has been determined that selected recipe information corresponding to the set control data has the identifier, transmitting the selected recipe information with the identifier, in association with a user ID of the information terminal apparatus, to the first server.

A cooker system according to another embodiment of the present disclosure includes the following: a cooker; a first server that collects information; a second server that provides recipe information indicating a cooking recipe used in the cooker; and an information terminal apparatus connectable to the first server and the second server, the information terminal apparatus being capable of controlling the cooker. The first server transmits, via a first network to the information terminal apparatus, first display data for causing a user of the information terminal apparatus to confirm a purpose of use of the recipe information and for asking the user for a permission to collect the recipe information. The first display data is displayed on a display of the information terminal apparatus. The second server transmits, via a second network to the information terminal apparatus, selected recipe information selected from among a plurality of items of recipe information on the information terminal apparatus and control data for the cooker for a preparation based on the selected recipe information, the plurality of items of recipe information including recipe information with an identifier indicating that the recipe information is for a food item related to a specific constitution, disorder, disease, or allergy. The information terminal apparatus displays the selected recipe information on the display of the information terminal apparatus. The information terminal apparatus sets the control data in the cooker by using the control data. In a case where it has been selected to permit collecting the recipe information for a purpose of use related to health care, out of the purpose of use on the information terminal apparatus using the first display data, and in a case where it has been determined that selected recipe information corresponding to the set control data has the identifier, the information terminal apparatus transmits the selected recipe information with the identifier, in association with a user ID of the information terminal apparatus, to the first server.

A cooker according to another embodiment of the present disclosure is used in the above-described cooker system.

A cooker according to another embodiment of the present disclosure is a cooker in a cooker system including a first server that collects information, a second server that provides recipe information indicating a cooking recipe used in the cooker, an information terminal apparatus that connects to the first server and receives first display data for causing a user of the information terminal apparatus to confirm a purpose of use of the recipe information and for asking the user for a permission to collect the recipe information, and that connects to the second server and receives selected recipe information selected from among a plurality of items of recipe information on the information terminal apparatus and control data for the cooker for a preparation based on the selected recipe information, and the cooker controllable by the information terminal apparatus. The cooker includes the following: a controller that receives, from the information terminal apparatus, the control data received by the information terminal apparatus from the second server, and that sets the control data; and a heating unit controlled by the controller based on the set control data. The plurality of items of recipe information include recipe information with an identifier indicating that the recipe information is for a food item related to a specific constitution, disorder, disease, or allergy. In a case where it has been selected to permit collecting the recipe information for a purpose of use related to health care, out of the purpose of use on the information terminal apparatus using the first display data, and in a case where it has been determined that selected recipe information corresponding to the set control data has the identifier, the information terminal apparatus transmits the selected recipe information with the identifier, in association with a user ID of the information terminal apparatus, to the first server.

A control method according to another embodiment of the present disclosure is a method for controlling an information terminal apparatus connectable to a first server that collects information, to a second server that provides recipe information indicating a cooking recipe used in a cooker, and to a third server that manages control data for the cooker for a preparation corresponding to the recipe information. The method causes a computer of the information terminal apparatus to perform a process including: (1) receiving, from the first server via a first network, first display data for causing a user of the information terminal apparatus to confirm a purpose of use of the recipe information and for asking the user for a permission to collect the recipe information; (2) displaying the first display data on a display of the information terminal apparatus; (3) accessing the second server via a second network and receiving, from the second server, selected recipe information selected from among a plurality of items of recipe information on the information terminal apparatus and access information for accessing the third server in order to obtain control data corresponding to the selected recipe information, the plurality of items of recipe information including recipe information with an identifier indicating that the recipe information is for a food item related to a specific constitution, disorder, disease, or allergy; (4) displaying the selected recipe information on the display of the information terminal apparatus; (5) accessing, based on the access information, the third server via a third network, and receiving control data corresponding to the selected recipe information; (6) setting the received control data in the cooker by using the control data; and (7) in a case where it has been selected to permit collecting the recipe information for a purpose of use related to health care, out of the purpose of use on the information terminal apparatus using the first display data, and in a case where it has been determined that selected recipe information corresponding to the set control data has the identifier, transmitting the selected recipe information with the identifier, in association with a user ID of the information terminal apparatus, to the first server.

A computer program according to another embodiment of the present disclosure is used in an information terminal apparatus connectable to a first server that collects information, to a second server that provides recipe information indicating a cooking recipe used in a cooker, and to a third server that manages control data for the cooker for a preparation corresponding to the recipe information. The program causes a computer of the information terminal apparatus to perform a process including: (1) receiving, from the first server via a first network, first display data for causing a user of the information terminal apparatus to confirm a purpose of use of the recipe information and for asking the user for a permission to collect the recipe information; (2) displaying the first display data on a display of the information terminal apparatus; (3) accessing the second server via a second network and receiving, from the second server, selected recipe information selected from among a plurality of items of recipe information on the information terminal apparatus and access information for accessing the third server in order to obtain control data corresponding to the selected recipe information, the plurality of items of recipe information including recipe information with an identifier indicating that the recipe information is for a food item related to a specific constitution, disorder, disease, or allergy; (4) displaying the selected recipe information on the display of the information terminal apparatus; (5) accessing, based on the access information, the third server via a third network, and receiving control data corresponding to the selected recipe information; (6) setting the received control data in the cooker by using the control data; and (7) in a case where it has been selected to permit collecting the recipe information for a purpose of use related to health care, out of the purpose of use on the information terminal apparatus using the first display data, and in a case where it has been determined that selected recipe information corresponding to the set control data has the identifier, transmitting the selected recipe information with the identifier, in association with a user ID of the information terminal apparatus, to the first server.

Hereinafter, an embodiment of the present disclosure will be specifically described.

3. Definitions of Terms

First, the definitions of terms used in the present specification will be described. In the present specification of the present application, the terms are defined as follows.

Cooker (or cooking home appliance): refers to an electrical appliance that performs a heating operation for cooking using electric power. An appliance such as a microwave oven, an electric rice cooker, or an induction-heating (IH) cooking heater corresponds to a cooker. A cooker is configured to set control data associated with recipe information for a food item, and to operate on the basis of the control data. The control data includes, for example, information of a control command that defines an operation mode of the appliance, such as output power and operation time. The control data can be generated by a server that manages and provides recipe information or another server operated in association with the former server, and can be set in the cooker via an information terminal apparatus.

Information terminal apparatus: refers to an information device that has a function of displaying information on a display and a communication function. Besides a device that includes a display, a device that displays information on an externally attached display corresponds to an information terminal apparatus. An information terminal apparatus may be, for example, a smartphone, a tablet terminal, a mobile phone, a notebook computer, a desktop computer, or a dedicated display terminal. In the present specification, when an information terminal apparatus is a mobile device, this device may be referred to as a "mobile terminal".

Server (or cloud server): refers to a computer or a recording medium that provides information to an information terminal apparatus via a network. A server includes a server that manages recipe information and that provides selected recipe information to an information terminal apparatus in response to a request from the information terminal apparatus, and a server that collects and utilizes recipe information selected by a user. The latter server has a function of transmitting, to an information terminal apparatus, display data for causing a user of the information terminal apparatus to confirm the purpose of use of recipe information and for asking the user for the permission to collect the recipe information. Typically, a server is realizable by a combination of a general computer and software (computer program) that performs the above-mentioned operation.

Display data: refers to arbitrary data for displaying information on a display. The data format is not restricted to a particular format, and display data may be, for example, data in Exchangeable Markup Language (XML) or Hypertext Markup Language (HTML), text data, or image data. "Display data" may be numeral data not conforming to an existing data format. When an information terminal apparatus configures a user interface that accepts and displays the numeral data, the numeral data can be referred to as "display data". In the present specification, displaying a screen based on display data may be represented as "displaying display data" for the sake of convenience.

Network: refers to a network configured by electric communication lines and includes the Internet, a private circuit, and a local area network (LAN). A plurality of types of networks may be combined, and wired or wireless networks may be used.

4. Basic Configuration Example

Next, a basic configuration example of the embodiment of the present disclosure will be described. In the following description, the same or similar components are given the same reference numeral.

FIG. 1A is a diagram illustrating an overview of the configuration of a cooker system according to an embodiment of the present disclosure. As illustrated in FIG. 1A, the cooker system includes an information terminal apparatus 300, a cooker (cooking home appliance) 400, a first server 500, and a second server 600.

The information terminal apparatus 300 is connectable to the first server 500, which collects information, via a first network (NW1). In addition, the information terminal apparatus 300 is connectable to the second server 600, which provides recipe information indicating a recipe to cook, which is used by the cooker 4, via a second network (NW2).

The first server 500 is a server for collecting information and utilizing the collected information for various services. Information collected by the first server 500 includes recipe information obtained, by a user of the information terminal apparatus 300, from the second server 600. Besides this, the first server 500 may be configured to collect log information, such as an operation history, from an information home appliance held by the user, for example.

The second server 600 is a server that manages recipe information for food items. Besides the recipe information, the second server 600 additionally manages control data, which is set in the cooker 400, in association with individual items of recipe information. In response to a request from the information terminal apparatus 300, the second server 600 provides recipe information and control data.

The information terminal apparatus 300 is a terminal held by a user and is used for obtaining recipe information and control data and for setting the control data in the cooker 400. By setting control data transmitted from the information terminal apparatus 300 in the cooker 400, the cooker 400 performs a heating operation that suits the preparation of a food item corresponding to the control data.

A computer of the information terminal apparatus 300 according to the embodiment executes the following operation by executing a computer program stored in a memory.

First, the computer receives, from the first server 500 via the first network, first display data for causing the user of the information terminal apparatus 300 to confirm the purpose of use of recipe information and for asking the user for the permission to collect recipe information, and displays a screen based on the first display data on the display of the information terminal apparatus 300. Accordingly, the user can confirm the purpose of use of recipe information and select, of his/her own will, whether or not to give the permission to the first server 500 to collect recipe information. The purpose of use of recipe information includes purposes related to health care. For example, the purpose of use included may be one that provides useful information or services to users in order to prevent specific constitutions, disorders, diseases, or allergies by collecting recipes related to these specific constitutions, disorders, diseases, or allergies.

In addition, the information terminal apparatus 300 accesses the second server 600 via the second network, and obtains a plurality of items of recipe information from the second server 600. Recipe information selected from among the plurality of items of recipe information on the information terminal apparatus 300 (referred to as "selected recipe information") and control data set in the cooker 400 for a preparation based on the selected recipe information are obtained from the second server 600. Here, the plurality of items of recipe information include recipe information having identifiers indicating that the recipes are for food items related to specific constitutions, disorders, diseases, or allergies. For example, recipe information for a food item that generally uses an egg but that uses a substitute ingredient includes an identifier indicating that the recipe is related to an egg allergy. In addition, recipe information for a low-calorie food item includes an identifier indicating that the recipe is related to a specific constitution, namely, weight control (diet). The information terminal apparatus 300 displays the selected recipe information on the display, and sets the control data in the cooker 400. Here, the timing to set the control data in the cooker 400 can be arbitrarily set by the user.

In the case where it has been selected to permit collecting recipe information for the purpose of use related to health care on a display screen based on the first display data, and in the case where it has been determined that selected recipe information corresponding to the set control data has the above-mentioned identifier, the information terminal apparatus 300 transmits the selected recipe information with the identifier, in association with the user ID of the information terminal apparatus 300, to the first server 500. Accordingly, in the case where it has been selected beforehand to permit collecting recipe information for the purpose of use related to health care, the first server 500 can collect recipe information with the identifier in association with the user ID. As a result, necessary information can be collected within a range in accordance with the purpose of use, without collecting unnecessary information from the user.

FIG. 1B is a diagram illustrating an overview of the configuration of a cooker system according to another embodiment of the present disclosure. The cooker system includes the information terminal apparatus 300, the cooker 400, the first server 500, the second server 600, and a third server 700. This embodiment has a configuration in which, of the functions of the second server 600 in the system illustrated in FIG. 1A, the function of managing and providing control data is separated to the third server 700. Such a configuration may be adopted in the case where, for example, provision of recipe information using the second server 600 and provision of control data for the cooker 400 using the third server 700 are performed by different providers. In this case, the information terminal apparatus 300 is connectable to the first server 500, which collects information, the second server 600, which provides recipe information indicating a recipe to cook used in the cooker 400, and the third server 700, which manages control data for the cooker 400 for a preparation corresponding to recipe information. The first server 500, the second server 600, and the third server 700 are capable of communicating with the information terminal apparatus 300 via the first network (NW1), the second network (NW2), and a third network (NW3), respectively.

The computer of the information terminal apparatus 300 in this embodiment executes the following operation by executing a computer program stored in a memory.

First, as in the above-described example, the computer receives, from the first server 500 via the first network, first display data for causing the user of the information terminal apparatus 300 to confirm the purpose of use of recipe information and for asking the user for the permission to collect recipe information, and displays a screen based on the first display data on the display of the information terminal apparatus 300. Accordingly, the user can confirm the purpose of use of recipe information and select, of his/her own will, whether or not to give the permission to the first server 500 to collect recipe information.

In addition, the information terminal apparatus 300 accesses the second server 600 via the second network, and obtains selected recipe information selected from among a plurality of items of recipe information on the information terminal apparatus 300, and access information for accessing the third server 700 in order to obtain control data corresponding to the selected recipe information. Here, as in the example illustrated in FIG. 1A, the plurality of items of recipe information include recipe information having identifiers indicating that the recipes are for food items related to specific constitutions, disorders, diseases, or allergies. The information terminal apparatus 300 displays the selected recipe information on the display. In addition, the information terminal apparatus 300 accesses the third server 700 via the third network on the basis of the above-mentioned access information for accessing the third server 700, and receives control data corresponding to the above-mentioned selected recipe information. Thereafter, the information terminal apparatus 300 sets the control data in the cooker 400.

Also in this embodiment, in the case where it has been selected to permit collecting recipe information for the purpose of use related to health care on a display screen based on the first display data, and in the case where it has been determined that selected recipe information corresponding to the set control data has the above-mentioned identifier, the information terminal apparatus 300 transmits the selected recipe information with the identifier, in association with the user ID of the information terminal apparatus 300, to the first server 500. Accordingly, in the case where it has been selected beforehand to permit collecting recipe information for the purpose of use related to health care, the first server 500 can collect recipe information with the identifier in association with the user ID. As a result, necessary information can be collected within a range in accordance with the purpose of use, without collecting unnecessary information from the user.

Note that the distribution of the functions of the first server 500, the second server 600, and the third server 700 is not limited to the above-described example, and various implementations are possible. For example, the functions of the three servers 500, 600, and 700 can be collected in a single server, or the functions of one server can be decentralized among multiple servers. Even with such a configuration, components (part of the computer, or a set of multiple computers) with the individual functions of the above-described first server 500, second server 600, and third server 700 can be interpreted as a single server. In addition, part or the entirety of the above-mentioned first network, second network, and third network can be made common. For example, in the case where one server computer has all the functions of the first to third servers 500, 600, and 700, the first to third networks may be one and the same network.

Hereinafter, a more specific embodiment of the present disclosure will be described.

5. First Embodiment

5.1. Configuration

FIG. 2 is a diagram schematically illustrating the configuration of a cooker system according to a first embodiment of the present disclosure. As illustrated in FIG. 2, the cooker system according to this embodiment includes the mobile terminal 300, the cooking home appliance 400, and a server 501. In this embodiment, the server 501 has the functions of both the first server 500 and the second server 600 in the above-described configuration illustrated in FIG. 1A.

The server 501 is a computer operated by a provider that provides a cloud service, and is located in a building or a data center, for example, managed by the provider. The server 501 collects information from the mobile terminal 300 via a network (NW), and provides a service based on the collected information to the user of the mobile terminal 300. Although not illustrated in FIG. 2, the cooking home appliance 400 and another home appliance owned by the user may be configured to transmit their log information to the server 501 via a home gateway. The server 501 collects the log information, and recipe information obtained by the user, accumulates the collected information in a database (DB) 510, and utilizes the information. In addition, the server 501 accumulates recipe information and control data used for the cooking home appliance 400. In response to an access by the user using the mobile terminal 300, the server 501 provides selected recipe information, and control data corresponding thereto. In providing the recipe information, the server 501 operates as, for example, a web server.

The mobile terminal 300 is an information device such as a smartphone. The mobile terminal 300 is capable of accessing the server 501 via a network. In addition, the mobile terminal 300 is capable of communicating with the cooking home appliance 400 via near field communication (NFC). When the mobile terminal 300 obtains display data by using a method such as logging in to a dedicated web site provided by the server 501, the mobile terminal 300 displays a display screen based on the display data on a built-in or external display. Accordingly, it becomes possible for the user to confirm the purpose of providing recipe information and to set whether or not to permit providing recipe information.

The cooking home appliance 400 is, for example, a microwave oven having an NFC tag. The cooking home appliance 400 performs near field communication with the mobile terminal 300, thereby obtaining control data (control command) from the mobile terminal 300 and setting the control data. Accordingly, the cooking home appliance 400 can execute a heating operation based on the control data.

FIG. 3 is a block diagram illustrating the configuration of the server 501. The server 501 includes, besides the database 510, a processing circuit 520 and a communication circuit 530.

The database 510 includes a recipe database (recipe DB) 512 that stores recipe information for food items, a history database (history DB) 514 that stores information regarding the use histories of users, a personal information database (personal information DB) 516 that stores personal information of users, and a collection permission database (permission DB) 518 that stores information of setting of whether or not collecting recipe information is permitted. These databases may be configured in a recording medium such as a hard disk using a known database management system.

The processing circuit 520 is a circuit that controls the overall operation of the server 501. The processing circuit 520 may be typically realized by a combination of a central processing unit (CPU) and a memory storing a computer program (hereinafter may simply be referred to as a "program"). By executing a command group written in the program expanded in the memory, the CPU can realize various functions described later. Note that the processing circuit 520 may be realized as hardware such as a digital signal processor (DSP) in which a computer program is embedded in a single semiconductor circuit.

The processing circuit 520 includes a screen generator 526 that generates display data to be displayed on the display of the mobile terminal 300, a control command generator 527 that generates a control command for controlling the cooking home appliance 400, and a DB updating unit 528 that updates the database 510. It is not necessary for these function units to be physically separated. For example, a CPU executing a program may be configured to operate as any of the function units in accordance with a processing timing.

The communication circuit 530 is a circuit that performs communication with another communication device via a network. The communication circuit 530 performs communication that conforms to, for example, the Ethernet (registered trademark) standard. Accordingly, the server 501 can communicate with the mobile terminal 300 and another home appliance.

The server 501 may include other components such as a function unit for collecting, editing, and providing log information of a home appliance, a graphic controller, a user interface, and a power supply circuit. However, since such components are not necessarily needed for the understanding of this embodiment, descriptions thereof are omitted.

Figure 4:
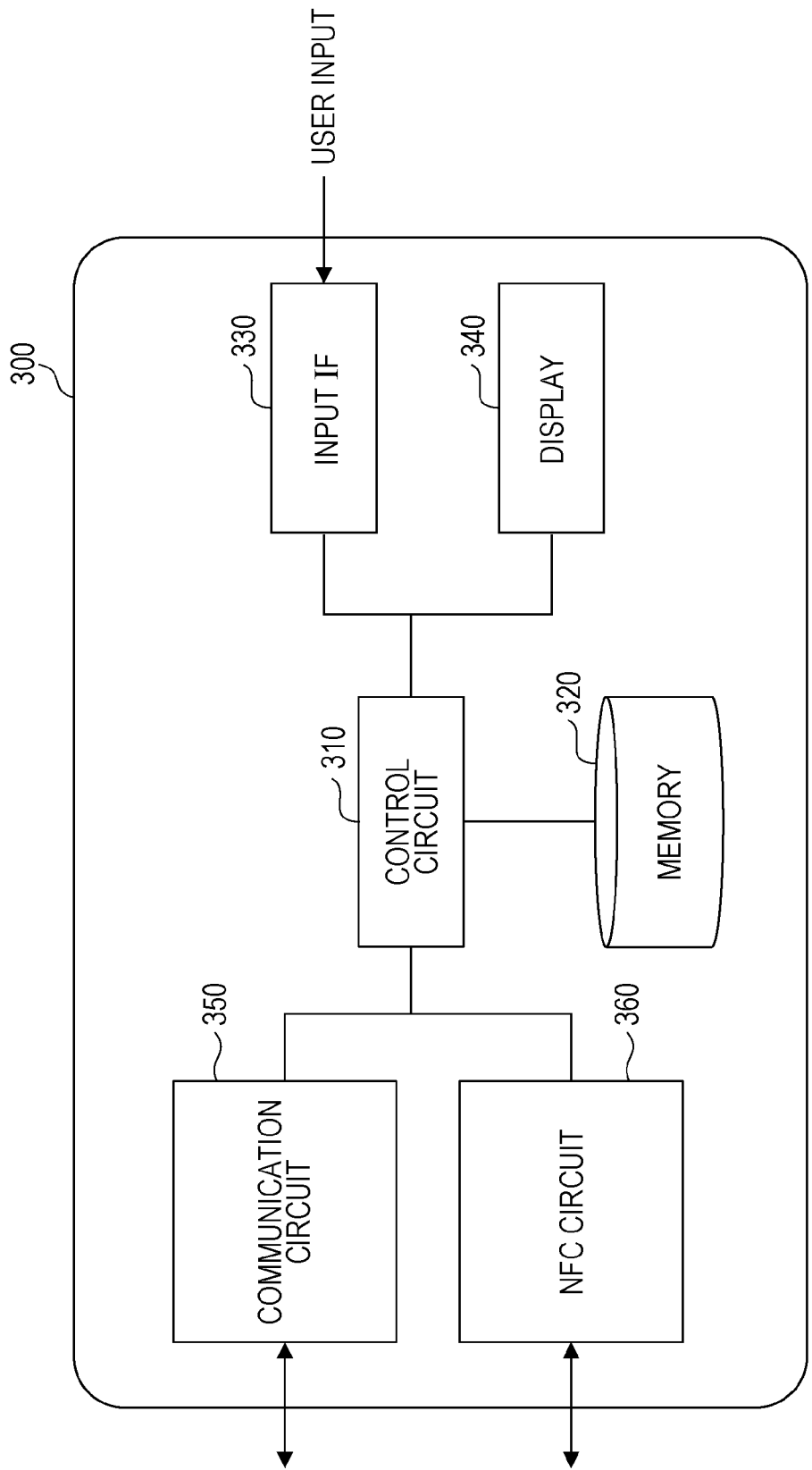
FIG. 4 is a block diagram illustrating the configuration of a mobile terminal.

FIG. 4 is a block diagram illustrating the configuration of the mobile terminal 300. The mobile terminal 300 includes an input interface (IF) 330, a display 340, a communication circuit 350, a near field communication (NFC) circuit 360, a control circuit 310, and a memory 320.

The input interface 330 is a device that accepts an input from the user, and may be, for example, a touch screen, a hardware button, a keyboard, a mouse, or any combination thereof. The display 340 is a device that displays a requested image in response to a command from the control circuit 310. The display 340 may be realized by, for example, liquid crystal or organic electroluminecence (EL). In the case where a touch screen is adopted as the display 340, the display 340 also serves the functions of the input interface 330.

The communication circuit 350 is a circuit that performs communication with another communication (such as the communication circuit 530 in the server 501) via a network. The communication circuit 350 performs communication that conforms to, for example, the Ethernet (registered trademark) standard. The NFC circuit 360 is a circuit that communicates with the cooking home appliance 400 via NFC. Accordingly, the mobile terminal 300 can be caused to function as an NFC reader/writer.

The control circuit 310 is a circuit (processor) that controls the overall operation of the mobile terminal 300, and may be realized by, for example, a CPU. By executing a command group written in a program expanded in the memory 320, the above-mentioned CPU can realize various functions. A command group for realizing the later-described operation of the mobile terminal 300 is written in a compute program. The program may be transmitted as an application through electric communication lines such as the Internet. Alternatively, the program may be recorded in a recording medium such as a compact-disc read-only memory (CD-ROM) and may be distributed as a product in the market. The control circuit 310 may be realized by hardware such as a DSP in which a computer program is embedded in a single semiconductor circuit.

The mobile terminal 300 may include components other than those illustrated in FIG. 4. However, since such components are not particularly needed for the understanding of this embodiment, descriptions thereof are omitted.

Figure 5:
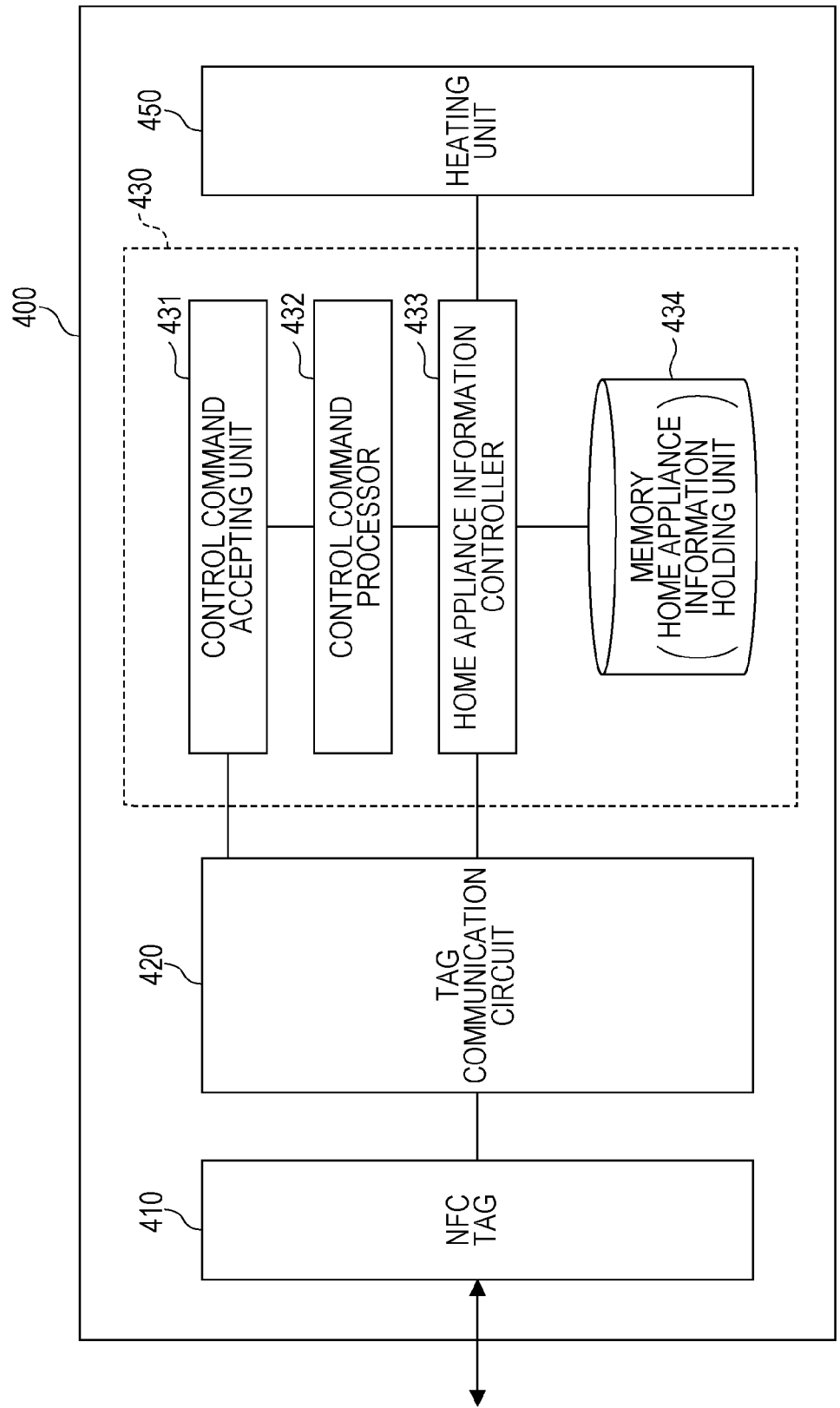
FIG. 5 is a block diagram illustrating the configuration of a cooking home appliance.

FIG. 5 is a block diagram illustrating the configuration of the cooking home appliance 400. The cooking home appliance 400 includes an NFC tag 410, a tag communication circuit 420, a processing circuit 430, and a heating unit 450.

The NFC tag 410 is an integrated circuit (IC) chip for performing NFC with the NFC circuit 360 of the mobile terminal 300. With the NFC tag 410, the cooking home appliance 400 can detect the approaching of the mobile terminal 300 and receive control data from the mobile terminal 300. The tag communication circuit 420 is a circuit for performing serial communication between the NFC tag 410 and the processing circuit 430.

The processing circuit 430 is a circuit that controls the operation of the cooking home appliance 400, and may be realized by, for example, a microcomputer. The processing circuit 430 includes a control command accepting unit 431, a control command processor 432, a home appliance information controller 433, and a memory (home appliance information holding unit) 434.

The control command accepting unit 431 accepts a control command from the tag communication circuit 420, and transfers the control command to the control command processor 432. The control command processor 432 determines the details of processing in accordance with the details of the control command, and notifies the home appliance information controller 433 thereof. For example, in the case where the control command is a write command, the control command processor 432 determines the details of processing in accordance with the details of the write command, such as the details of operation of heating with an output of 1000 W for ten minutes. In contrast, in the case where the control command is a read command, the control command processor 432 determines the details of processing, such as obtaining information, such as a device operation history stored in the memory 434. The home appliance information controller 433 controls the heating unit 450 or records the device operation history in the memory 434 on the basis of the details of processing determined by the control command processor 432. In addition, in response to issuing of a read command, information indicating the operation history stored in the memory 434 is transmitted to the mobile terminal 300 via the tag communication circuit 420 and the NFC tag 410.

The heating unit 450 performs a heating operation for cooking in accordance with a command from the home appliance information controller 433. In the case where the cooking home appliance 400 is, for example, a microwave oven, the heating unit 450 includes a circuit including, for example, a magnetron that generates microwaves and an inverter that controls the generation of microwaves. In addition, in the case where the cooking home appliance 400 is, for example, an electromagnetic cooker, the heating unit 450 includes a circuit including, for example, a coil that performs induction heating and an inverter that controls the induction heating. As described above, the heating unit 450 may have various embodiments in accordance with the type of cooking home appliance 400; these embodiments are common in the point that they perform a heating operation for cooking in accordance with a control command.

The cooking home appliance 400 may include components other than those illustrated in FIG. 5. However, since such components are not particularly needed for the understanding of this embodiment, descriptions thereof are omitted.

Although it is assumed in this embodiment that NFC is performed between the cooking home appliance 400 and the mobile terminal 300, instead of NFC, another wireless communication scheme such as Bluetooth (registered trademark) or Wi-Fi (registered trademark) may be adopted.

5.2. Operation

Next, the operation of the cooker system according to this embodiment will be described. In the cooker system according to this embodiment, a user registration process, a recipe information providing purpose confirmation process, and a recipe information providing process are performed. Hereinafter, these processes will be specifically described.

5.2.1. User Registration Process

Figure 6:
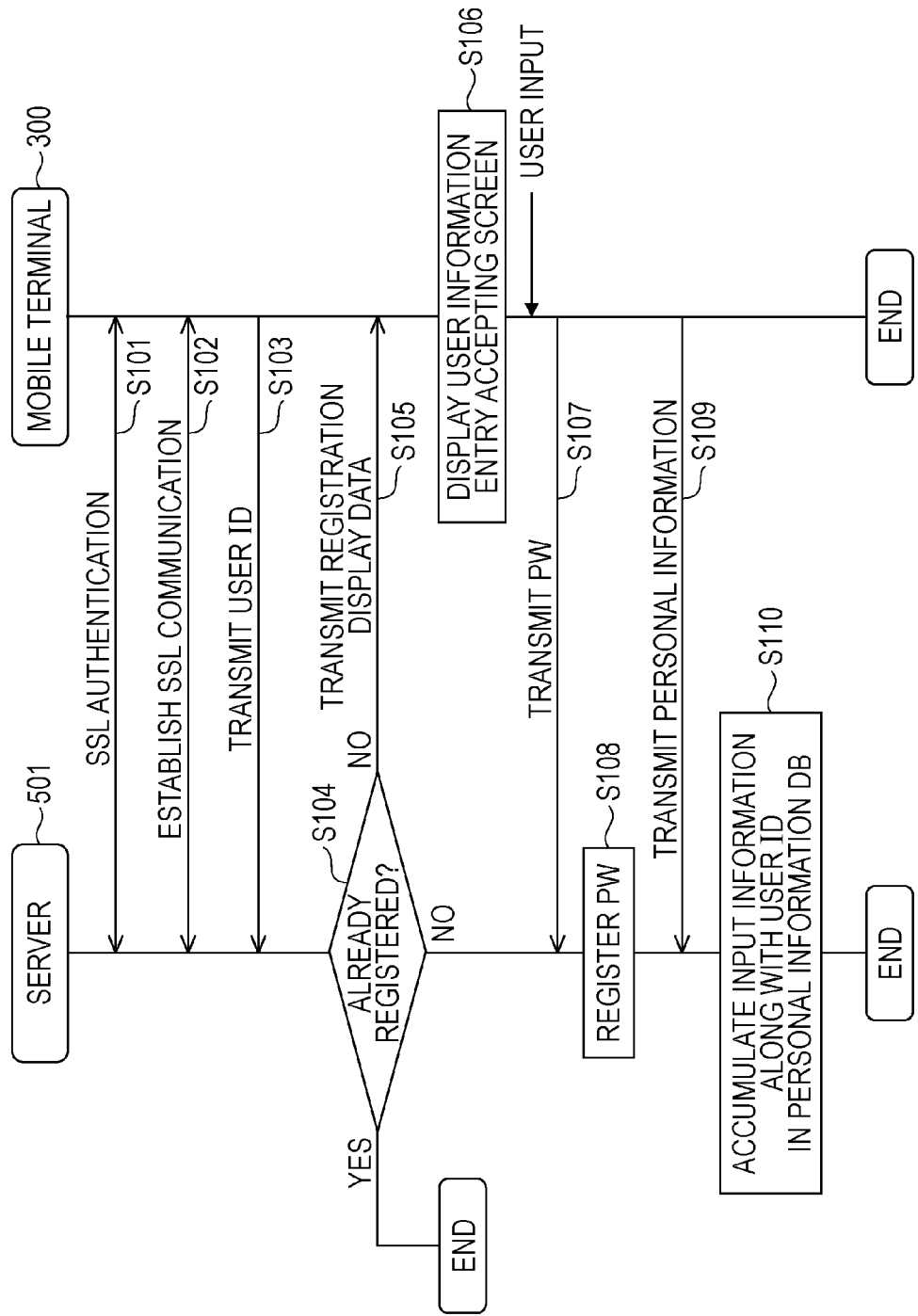
FIG. 6 is a flowchart illustrating a user registration process performed between the server and the mobile terminal.

FIG. 6 is a flowchart illustrating a user registration process performed between the server 501 and the mobile terminal 300. This process is executed when a user uses this service for the first time.

First, when the mobile terminal 300 accesses a web site provided by the server 501 or activates an application for this service by using a browser, for example, Secure Sockets Layer (SSL) authentication is performed between the server 501 and the mobile terminal 300 (step S101). When SSL communication is established (step S102), the mobile terminal 300 transmits a user ID to the server 501 (step S103). The server 501, which has received the user ID, determines whether the transmitted user ID has already been registered in the personal information DB 516 (step S104). Here, when it is determined that the user ID has already been registered, the server 501 ends the user registration process. In this case, for example, the server 501 transmits a notification indicating that the user registration has been already completed to the mobile terminal 300. In contrast, when it is determined that the user ID has not been registered yet, the server 501 generates display data for performing registration, and transmits the display data to the mobile terminal 300 (step S105).

The mobile terminal 300, which has received the display data, displays a user information entry accepting screen on the display 340 (step S106). When the user enters a password (PW) and personal information on the screen, the mobile terminal 300 first transmits the password to the server 501 (step S107). The server 501 registers the transmitted password (step S108). Next, the mobile terminal 300 transmits the entered personal information to the server 501 (step S109). The server 501, which has received the personal information, accumulates the personal information in association with the user ID in the personal information DB 516 (step S110).

FIG. 7 is a diagram illustrating an example of personal information accumulated in the personal information DB 516. The personal information DB 516 has a table structure storing a user ID and personal information in an associated manner. Personal information includes information such as the name, address, date of birth, sex, email address, and hobby. The configuration of the personal information DB 516 may be different from that illustrated in FIG. 7.

With the above process, the user registration is completed. Thereafter, the user can use the service according to this embodiment. Although the user registration is performed from the mobile terminal 300 in the above-described example, the user registration may be performed from, for example, the browser of a personal computer (PC).

5.2.2. Providing Purpose Confirmation Process

Next, the recipe information providing purpose confirmation process will be described. The server 501 generates display data for causing a user to confirm the purpose of use of recipe information selected by the user and for asking the user for the permission to collect recipe information, and transmits the display data to the mobile terminal 300. Accordingly, the user can be informed of the purpose of use of recipe information and can select, of his/her own will, whether or not to give the permission to collect recipe information. This process may be executed at a certain timing, such as immediately after the above-described user registration process, or when registration of a new device is performed.

Figure 8:
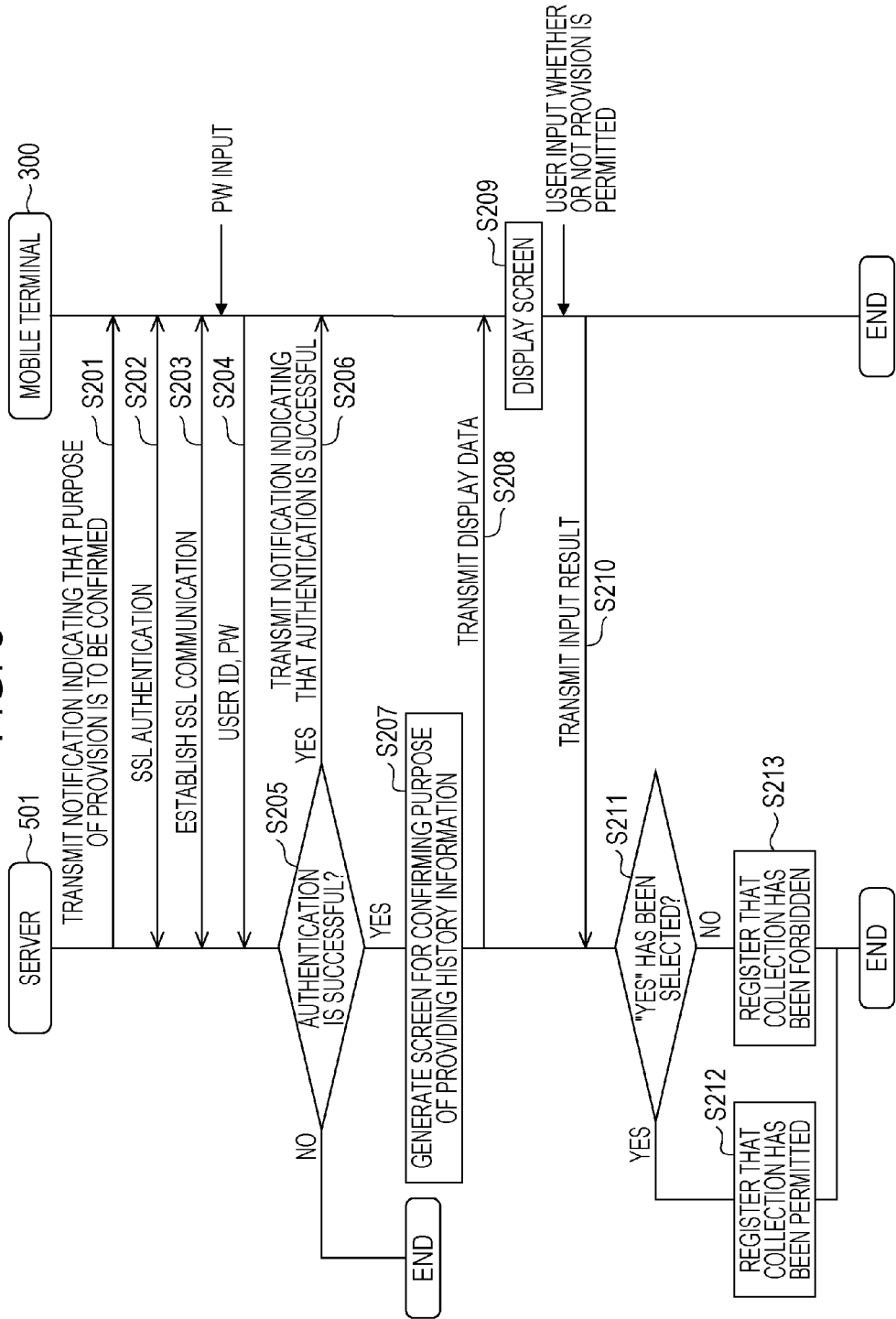
FIG. 8 is a flowchart illustrating a process of confirming the purpose of provision of recipe information.

FIG. 8 is a flowchart illustrating the recipe information providing purpose confirmation process. First, the server 501 transmits, to the mobile terminal 300, a notification indicating that a process of confirming the purpose of providing recipe information is to be performed (step S201). Next, the server 501 and the mobile terminal 300 perform SSL authentication (step S202). When SSL communication is established (step S203), the mobile terminal 300 displays a screen for prompting the user to enter a password (PW). When a password is entered by the user, the mobile terminal 300 transmits the user ID and the password to the server 501 (step S204). On the basis of the transmitted user ID and password, the server 501 performs authentication (step S205). When authentication fails, the providing purpose confirmation process ends. When authentication is successful, the server 501 transmits, to the mobile terminal 300, a notification indicating that authentication has been normally performed (authentication OK) (step S206). In addition, the server 501 generates display data for displaying a screen for causing the user to confirm the purpose of providing history information (providing purpose confirmation screen) (step S207), and transmits the display data to the mobile terminal 300 (step S208).

The providing purpose confirmation screen functions as a screen that causes the user of the mobile terminal 300 to confirm the purpose of use of recipe information, and asks the user for the permission to collect recipe information. Therefore, the above-described display data corresponds to "first display data" that causes the user of the mobile terminal 300 to confirm the purpose of use of recipe information and asks the user for the permission to collect recipe information. When the mobile terminal 300 receives the display data, the mobile terminal 300 displays a screen based on the display data on the display 340 (step S209).

FIG. 9 is a diagram illustrating an example of a providing purpose confirmation screen. In this example, a screen that causes the user to confirm that the purpose of use of recipe information resides in collecting and utilizing allergy-related information, and asks the user for the permission to collect the related recipe information. The user selects "yes" or "no" using the mobile terminal 300, thereby selecting whether or not to give the permission to collect recipe information. In this exemplary screen, an item for specifying a recipe information providing period is additionally displayed. The user selects one of "30 days", "180 days", and "unlimited", thereby specifying a providing period. In this manner, the display data may additionally include an item for specifying a recipe information providing period.

When the user presses a "send" button on the providing purpose confirmation screen, the mobile terminal 300 transmits information indicating the input result to the server 501 (step S210 in FIG. 8). In response to this, the server 501 determines whether the input result is "yes" or "no" on the basis of the information (step S211). When it is determined that "yes" has been selected, the server 501 registers the fact that recipe information is collectable in the permission DB 518 (step S212). In contrast, when "no" has been selected, the server 501 registers the fact that collecting recipe information has been denied in the permission DB 518 (step S213).

FIG. 10 is a diagram illustrating an example of information stored in the permission DB 518. As illustrated in FIG. 10, the permission DB 518 stores information indicating whether or not collection is permitted, for each purpose of use associated with a user ID. For example, regarding the purpose of use related to health care, information indicating whether or not collection is permitted, and a providing period are recorded for each of items, such as allergy-related, weight-control-related, and specific-disease-related. Besides the purpose related to health care, information regarding other purposes such as for the advertisement purpose may additionally be recorded. Note that the configuration of the permission DB 518 is not limited to that illustrated in FIG. 10. For example, whether or not collection is permitted and a providing period may be managed in larger units, such as the health care purpose and the advertisement purpose, or may be managed in units of further fragmented items.

With the above process, setting indicating whether or not providing recipe information is permitted is completed. Thereafter, the mobile terminal 300 determines whether or not to provide selected recipe information to the server 501 on the basis of the details of this setting.

Note that the mobile terminal 300 may display, in addition to the providing confirmation screen illustrated in FIG. 9, a screen for setting a more detailed providing condition. For example, after "yes" is selected on the screen illustrated in FIG. 9, the screen may change to that illustrated in FIG. 11. On the screen illustrated in FIG. 11, the purpose of use of collected recipe information is indicated in more details. For example, a screen asking a user who has an allergy for the permission to send an ad is displayed. Here, the user selects "yes" or "no", thereby determining whether an ad related to the allergy is to be provided to the user. In addition, in the example illustrated in FIG. 11, a link to a screen displaying more detailed information on various services that can be provided to the user is displayed in a lower portion of the screen. Yet more detailed information may be displayed by pressing such a link by the user.

5.2.3. Recipe Information Providing Process

Next, a process of obtaining, by the user, recipe information and control data from the server 501 by using the mobile terminal 300, and setting the control data in the cooking home appliance 400 will be described. This process includes a process of determining, by the mobile terminal 300, whether or not to provide selected recipe information to the server 501 on the basis of the above-mentioned setting indicating whether or not collecting recipe information is permitted.

Figure 12:
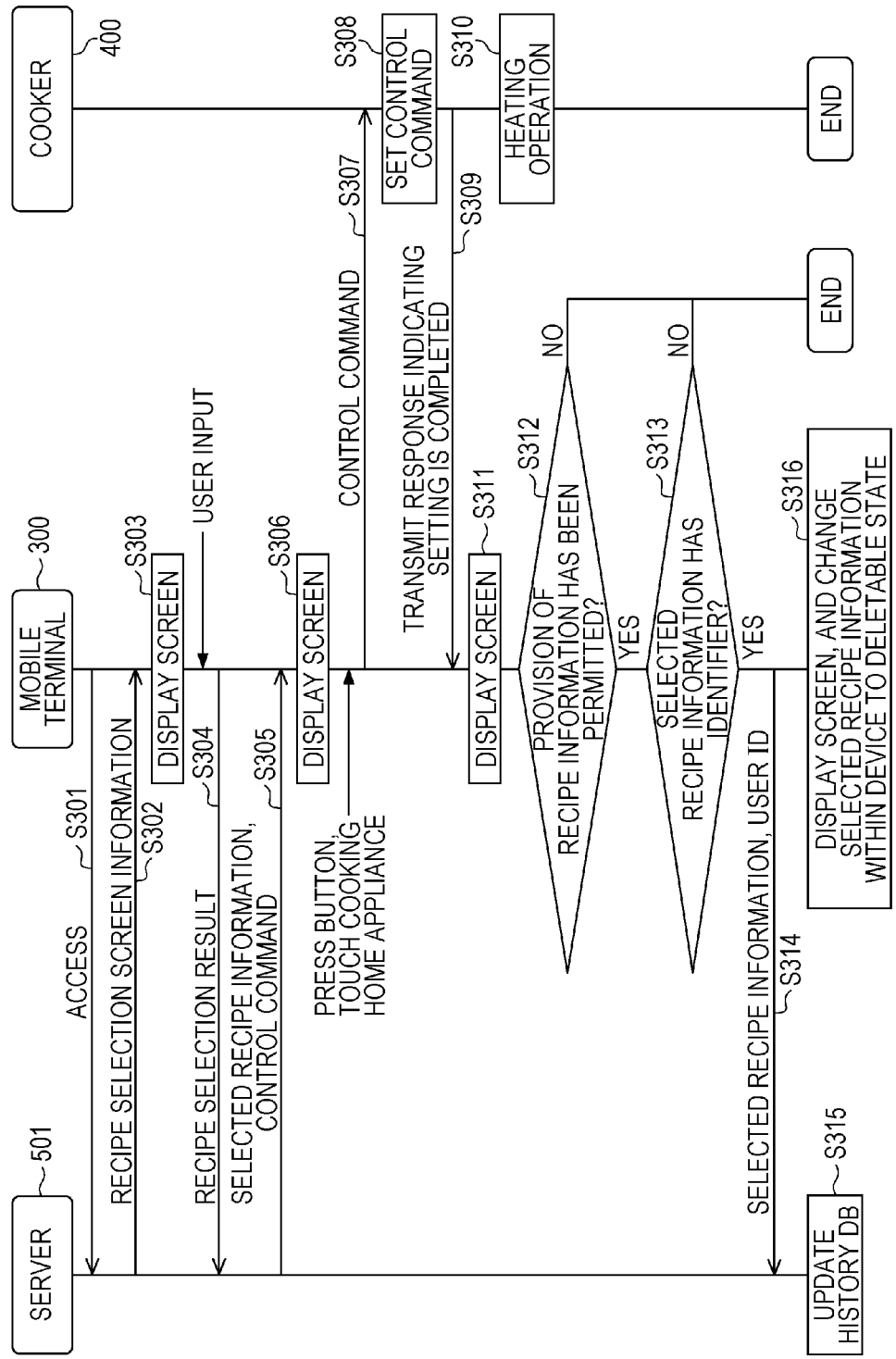
FIG. 12 is a flowchart illustrating a process of obtaining, by a user, recipe information and control data from the server by using the mobile terminal, and setting the control data in the cooking home appliance.

FIG. 12 is a flowchart illustrating this process. First, the mobile terminal 300 accesses the server 501 in accordance with an operation performed by the user (step S301). Here, the term "access" refers to, for example, activating an application, logging in to a web site introducing recipes for food items provided by the server 501, and giving a request for a recipe selection screen. In response to this request, the server 501 generates display data for displaying a recipe selection screen on the basis of information stored in the recipe DB 512, and transmits the display data to the mobile terminal 300 (step S302). Upon receipt of this, the mobile terminal 300 displays the recipe selection screen on the display 340 (step S303). The recipe selection screen includes a plurality of items of recipe information. An example of the recipe selection screen will be described later. Here, when the user selects desired recipe information, the mobile terminal 300 transmits information indicating the selected result to the server 501 (step S304). Upon receipt of this, the server 501 obtains information for displaying a screen of the selected recipe (selected recipe information) and control data used for the preparation of that recipe (control command) from the recipe DB 512, and transmits the obtained information and control data to the mobile terminal 300 (step S305). In response to this, the mobile terminal 300 displays the received selected recipe information on the display 340 (step S306). Accordingly, the user can be informed of the details of the selected recipe.

FIG. 13 is a diagram illustrating an example of information stored in the recipe DB 512. In this example, the recipe DB 512 includes information such as a recipe ID, food item name, ingredients, identifier, and control data. Although the recipe DB 512 may additionally include information regarding the amount of each ingredient and the preparation procedure besides the above-mentioned items of information, these details are omitted in FIG. 13 for the sake of convenience. As in the second item of recipe information in FIG. 13, one item of recipe information may include a plurality of identifiers.

Here, an identifier is information indicating that the recipe is for a food item related to a specific constitution, disorder, disease, or allergy. The example illustrated in FIG. 13 includes the following identifiers: egg allergy, wheat allergy, low calories, and diabetes. In the present specification, a "specific constitution" may include not only the concept meaning a constitution itself, such as obesity, hypertension, and being likely to gain weight, but also the concept related to the improvement of specific constitutions, such as low calories, weight control, and diet.

Control data is data for controlling the operation of the cooking home appliance 400. As illustrated in FIG. 13, control data may include information such as a heating temperature, operation time, and output power. Control data may be saved in the form of a control command that is used as it is by the cooking home appliance 400, or may be saved in other formats that can be converted to a control command.

The recipe selection screen displayed in step S303 is generated on the basis of the above-described recipe DB 512.

FIG. 14 is a diagram illustrating an example of the recipe selection screen displayed in step S303. In this example, the recipe selection screen has a hierarchical structure classified by purpose and ingredient. For example, when the user selects the item "allergy" included in a purpose-classified menu on a screen illustrated in part (a) of FIG. 14, a screen is displayed on which the user can select which allergy with which recipes are related is to be provided, as illustrated in part (b) of FIG. 14. Here, when the user selects "egg" here, recipe candidates for users with an egg allergy are displayed, as illustrated in part (c) of FIG. 14.

Figure 15:
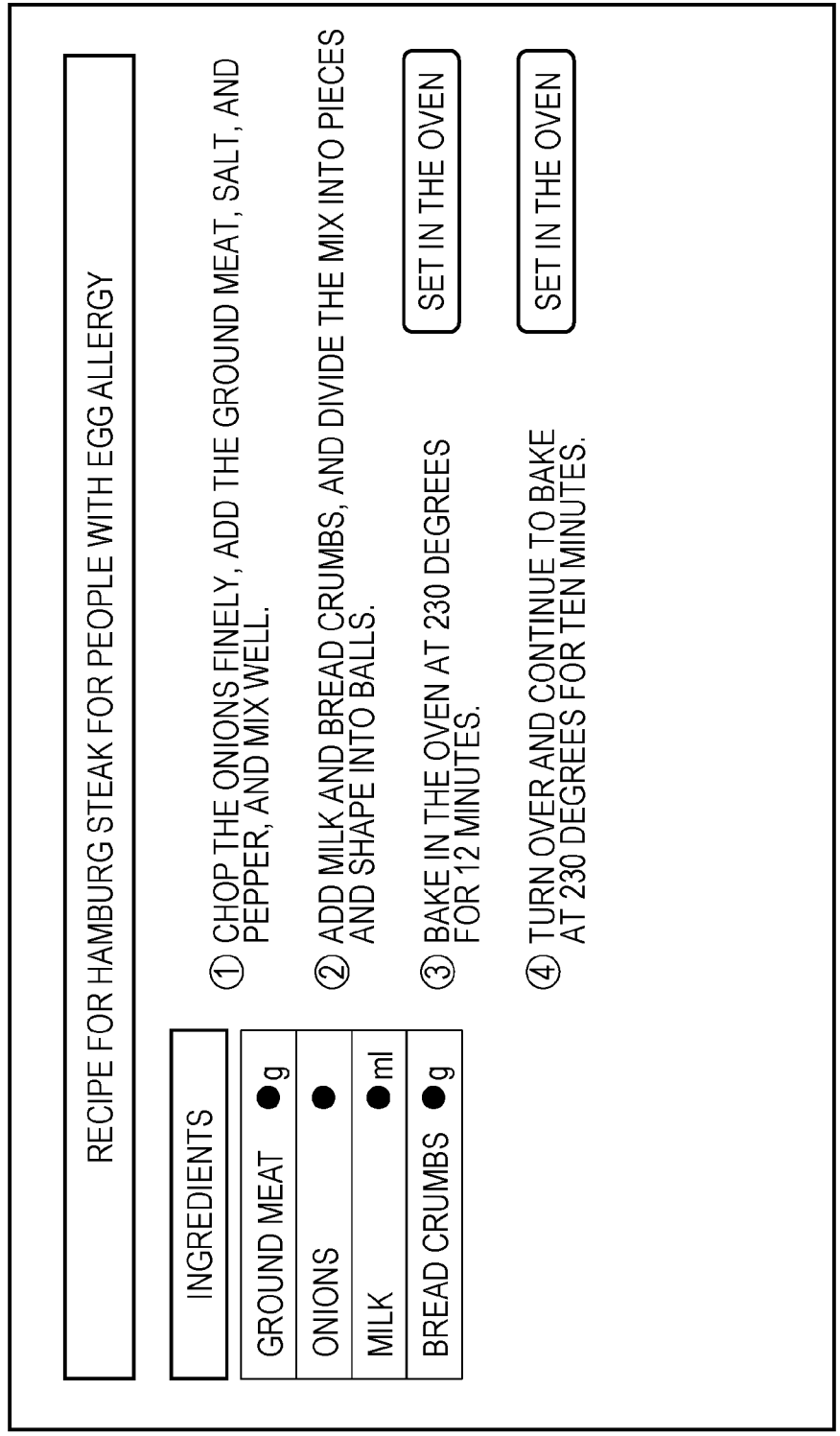
FIG. 15 is a diagram illustrating an exemplary screen indicating the details of selected recipe information.

FIG. 15 is a diagram illustrating an exemplary screen indicating the details of selected recipe information displayed in step S306. This screen is displayed in the case where "Hamburg steak" has been selected from among recipes illustrated in FIG. 14(*c*). As illustrated in FIG. 14(*c*), this screen includes display of ingredient information, the preparation procedure, and the button "set in the oven" for setting the control command in the cooking home appliance 400 (oven in this example) for each heating step.

Figure 16:
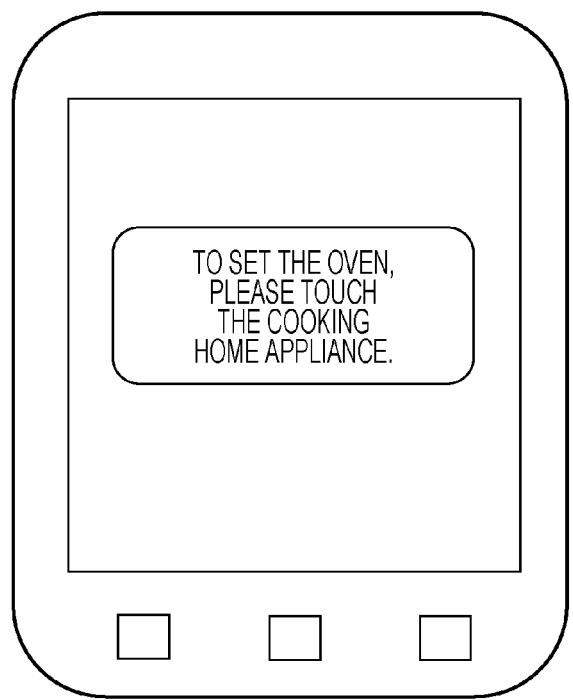
FIG. 16 is a diagram illustrating another exemplary screen prompting the user to touch the cooking home appliance.

When the user presses the button "set in the oven" in this state, the mobile terminal 300 displays a screen prompting the user to touch the cooking home appliance 400 with the mobile terminal 300 (or brings the mobile terminal 300 close to the cooking home appliance 400) on the display 340, as illustrated in FIG. 16, for example. When the user brings the mobile terminal 300 close to the cooking home appliance 400 in this state, the mobile terminal 300 transmits a control command to the cooking home appliance 400 (step S307 in FIG. 12). Upon receipt of this control command, the cooking home appliance 400 sets control parameters, such as an operation mode, heating temperature, operation time, and output power, in accordance with the details of the command (step S308). In the present specification, making such settings to enable execution of a heating operation is represented as "setting control data". When the setting is completed, the cooking home appliance 400 transmits a response indicating that the setting is completed (setting completion notification) to the mobile terminal 300 (step S309). Thereafter, the cooking home appliance 400 drives the heating unit 450 in accordance with the set details to perform a heating operation (step S310).

Figure 17:
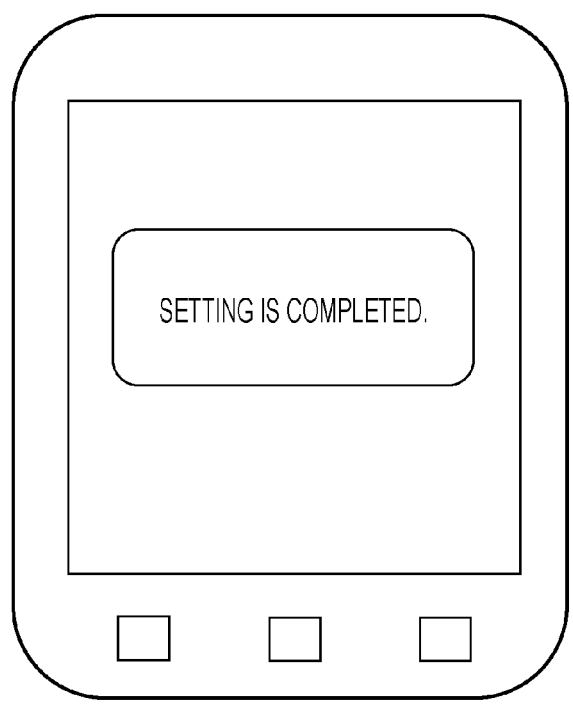
FIG. 17 is a diagram illustrating an exemplary screen indicating completion of the setting.
Figure 18:
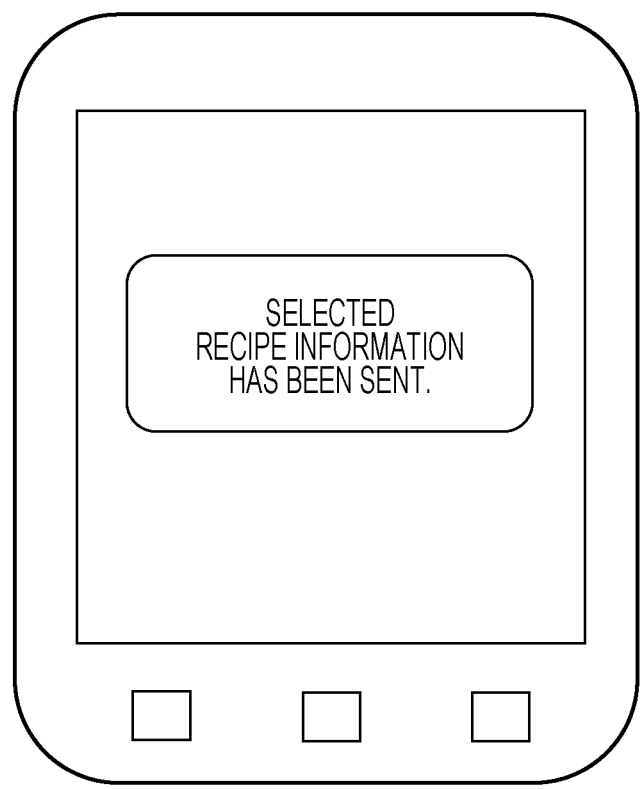
FIG. 18 is a diagram illustrating an exemplary screen indicating completion of transmission of the selected recipe information to the server.

Upon receipt of the setting completion notification, the mobile terminal 300 displays a screen indicating that the setting is completed on the display 340, as illustrated in FIG. 17, for example (step S311). The mobile terminal 300 determines whether or not provision of recipe information is permitted (step S312). This determination is performed on the basis of, for example, the details of the above-described permission DB 518. At this time, the mobile terminal 300 determines whether or not provision of recipe information is permitted by asking the server 501 for the details of the permission DB 518 or by saving beforehand information on whether or not collection is permitted. When it is determined that provision of recipe information is not permitted, the mobile terminal 300 ends the process without transmitting the selected recipe information to the server 501. In contrast, when it is determined that provision of recipe information is permitted, the mobile terminal 300 determines whether the selected recipe information includes an identifier indicating that the recipe is for a food item related to a specific constitution, disorder, disease, or allergy (step S313). When it is determined here that the selected recipe information does not include such an identifier, the mobile terminal 300 ends the process without transmitting the selected recipe information to the server 501. In contrast, when it is determined that the selected recipe information includes such an identifier, the mobile terminal 300 transmits the selected recipe information, which includes the identifier, in association with the user ID to the server 501 (step S314). Thereafter, the server 501 registers the received selected recipe information in association with the user ID in the history DB 514 (step S315). In addition, as illustrated in FIG. 18, the mobile terminal 300 displays a screen indicating that transmission is completed, and changes the selected recipe information stored in a memory in the mobile terminal 300 to a deletable state (step S316). Here, a "deletable state" refers to a state in which, though not deleted at that point, a deletion flag is added to the recipe information such that the recipe information will be deleted at the time this service application is ended. This can prevent such circumstances in which recipe information, whose setting in the cooking home appliance 400 and transmission to the server 501 are completed, remains in the memory and occupies the space of the memory after the application is ended.

FIG. 19 is a diagram illustrating an example of information recorded in the history DB 514. The history DB 514 includes information of a user ID, name, tag, recipe ID, and date. Selected recipe information is registered as "tag" and "recipe ID". Here, a tag is information corresponding to an identifier and may be information such as "egg" for an egg allergy and "wheat" for a wheat allergy. Using this tag information, the server 501 can detect that each user is interested in a specific constitution, disorder, disease, or allergy, and provide information or services that suit the user.

Note that the above-described process of changing the selected recipe information to a deletable state in step S316 may be performed prior to transmission of the selected recipe information in step S314. For example, this process may be performed immediately after step S307 or immediately after step S309. In addition, the selected recipe information may be deleted immediately without performing the process of changing the selected recipe information to a deletable state.

5.3. Advantageous Effects

With the above configuration and operation, the user of the mobile terminal 300 can easily obtain desired recipe information and perform the settings of a heating operation in the cooking home appliance 400. In addition, only in the case where the user permits beforehand collecting recipe information for the purpose of health care and selected recipe information has an identifier, the mobile terminal 300 performs automatic determination and transmits the selected recipe information to the server 501. Therefore, the burden of determining whether or not to provide the selected recipe information to the server 501 can be moderated, while the privacy can be protected.

In addition, in the case where the frequency of the server 501 receiving provision of selected recipe information with an identifier from the mobile terminal of a specific user is high, it can be estimated that the user is more or less interested in health care. Therefore, for example, information or services considered to be necessary for the user can be provided. In contrast, in the case where the frequency of the server 501 receiving provision of selected recipe information with an identifier from the mobile terminal of a specific user is low, it can be estimated that the user is in a relatively healthy state. Therefore, for example, information or services unnecessary for the user can be prevented from being provided to the user.

Further, it becomes possible to provide information or services in accordance with the specific details of selected recipe information with an identifier. Specifically, since it is possible to identify in which constitution, disorder, disease or allergy the user is interested, it becomes possible to provide information or services that is directly related with that interest. As a result, only information or services necessary for the user of the mobile terminal 300 can be provided to the user of the mobile terminal 300, and unnecessary information or services are prevented from uselessly provided to the user. For example, efficient information provision becomes possible in which, to a user who has an egg allergy, a wheat allergy, or the like, recipe information including no such allergen is provided, and no information unrelated to such an allergy is provided.

6. Other Embodiments

The present disclosure is not limited to the above-described embodiment, and various embodiments are conceivable. Hereinafter, other embodiments will be described.

FIG. 20 is a diagram illustrating another exemplary screen for setting whether or not collecting information is permitted. In this example, the case is assumed in which, not only recipe information is collected, but also information (log information) regarding the operation history of a home appliance is collected. As described here, a system may be configured to be capable of setting whether or not to permit log information related to allergies, such as the operation frequency information and information related to frequency of using allergen-inhibitory mode of an air purifier, and information of a used cooking mode(s), and information of a used food material(s) of a cooking home appliance.

Next, a specific embodiment corresponding to the configuration illustrated in FIG. 1A will be described.

Figure 21:
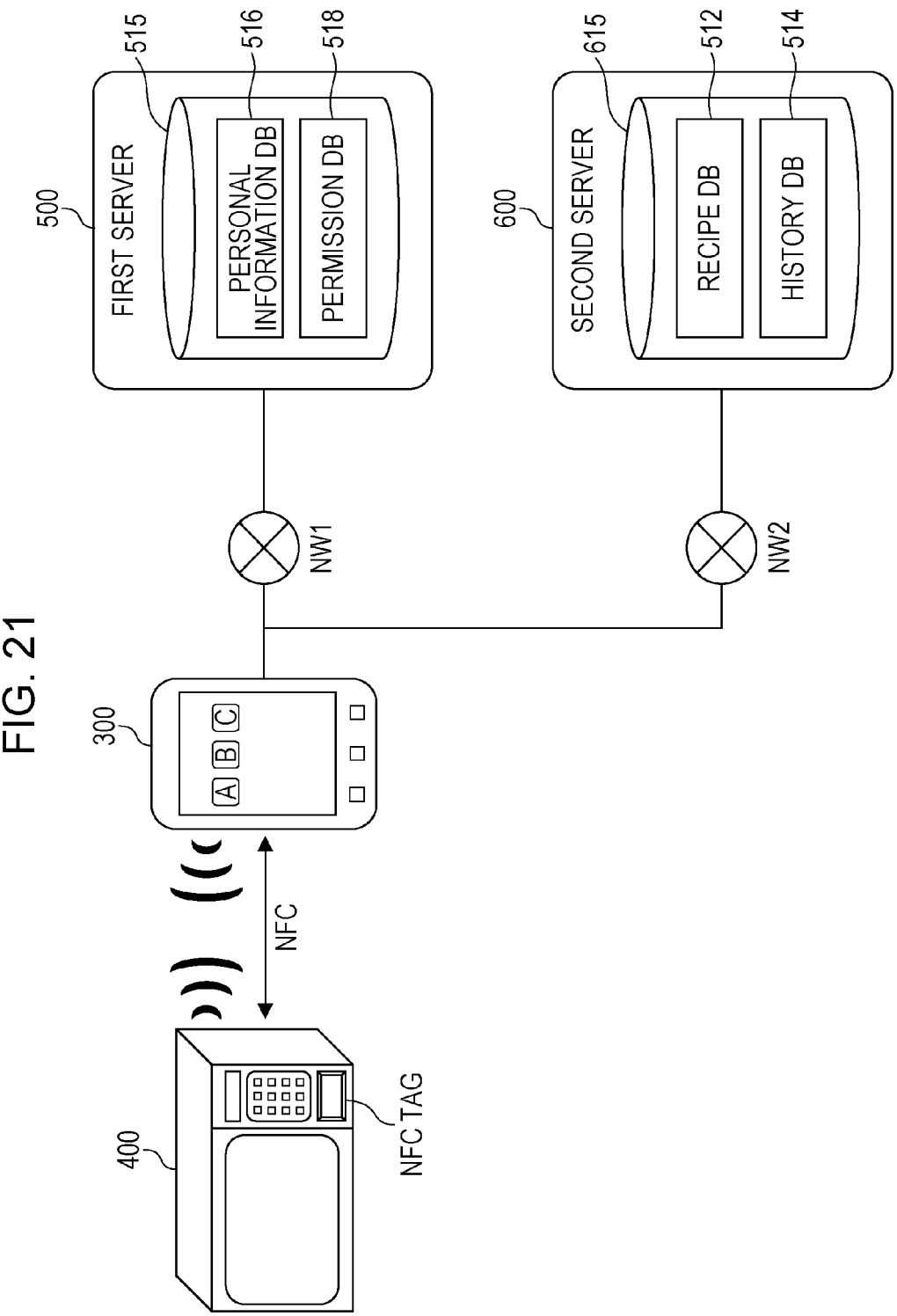
FIG. 21 is a diagram illustrating the configuration of an embodiment of a cooker system including two servers.

FIG. 21 is a diagram illustrating the configuration of an embodiment in which the functions of the server 501 according to the first embodiment are shared among two servers (first server 500 and second server 600). The mobile terminal 300 is connected to be communicable with the first server 500 via the first network (NW1) and is connected to be communicable with the second server 600 via the second network (NW2). The first server 500 includes a first database 515 including the personal information DB 516 and the permission DB 518. The second server 600 includes a second database 615 including the recipe DB 512 and the history DB 514. The first server 500 has the same configuration as the server 501 except for the point that the first server 500 does not include the recipe DB 512, the history DB 514, and the control command generator 527 illustrated in FIG. 3. In contrast, the second server 600 has the same configuration as the server 501 except for the point that the second server 600 does not include the personal information DB 516 and the permission DB 518 illustrated in FIG. 3. In this embodiment, the operation executed by the server 501 in FIGS. 6 and 8 is performed by the first server 500. In contrast, the operation executed by the server 501 in FIG. 12 is cooperatively performed by the first server 500 and the second server 600.

Figure 22:
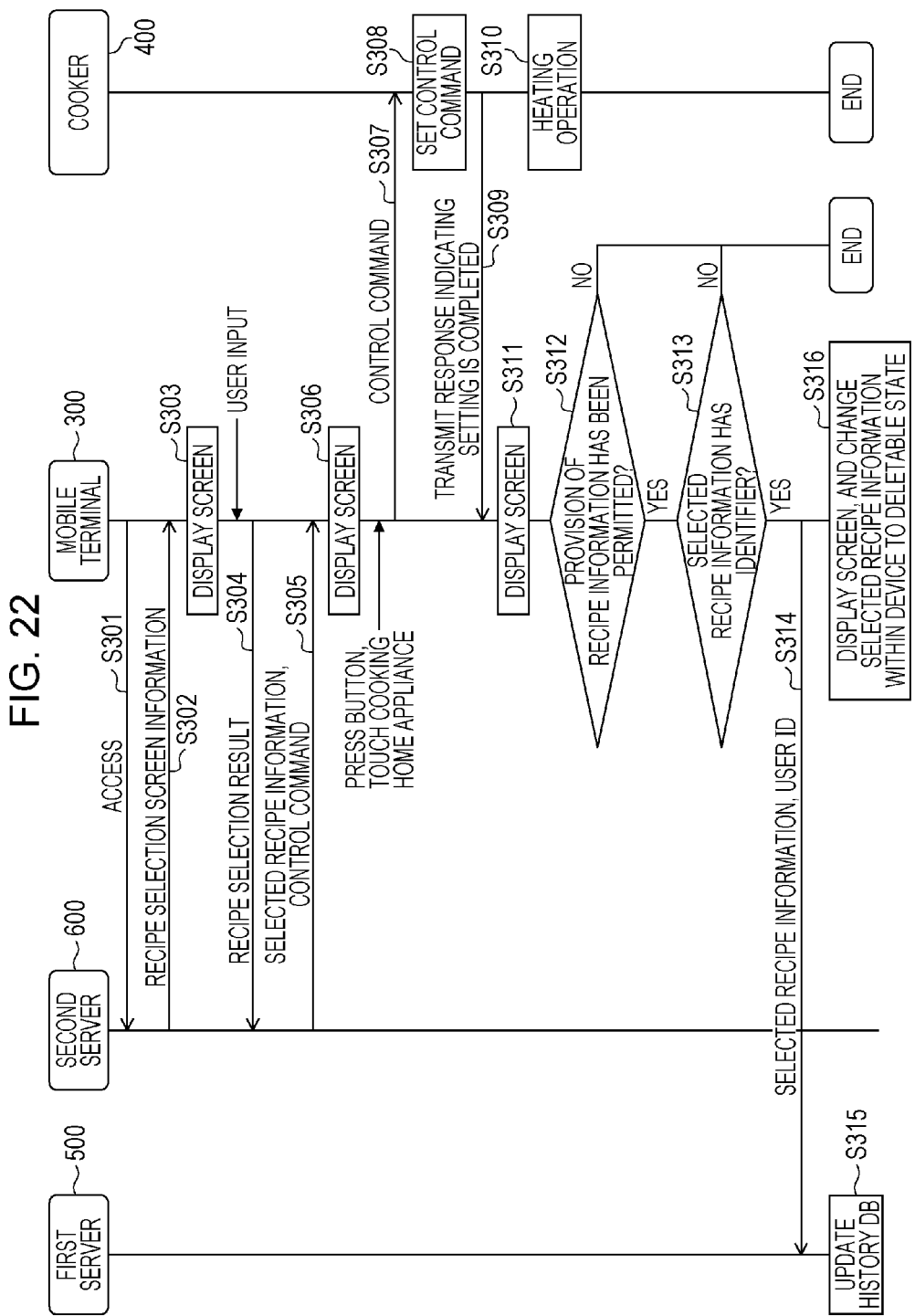
FIG. 22 is a flowchart illustrating a recipe information obtaining and transmitting process according to the embodiment illustrated in FIG. 21.

FIG. 22 is a flowchart illustrating a recipe information obtaining and transmitting process according to the embodiment illustrated in FIG. 21. The process illustrated in FIG. 22 is the same as the process illustrated in FIG. 12 except for the point that, of the operation of the server 500 in FIG. 12, the operation regarding provision of recipe information (steps S301, S302, S304, and S305) is executed by the second server 600, and the operation of registering selected recipe information in the history DB 514 (step S315) is executed by the first server 500.

With the above configuration, it is possible to realize a cooker system suitable for the case in which the first server 500, which collects information necessary for providing a cloud service from the mobile terminal 300 of the user, and the second server 600, which provides recipe information to the user, are operated by different providers.

Next, a specific embodiment corresponding to FIG. 1B will be described.

FIG. 23 is a diagram illustrating the configuration of an embodiment in which the functions of the server 501 according to the first embodiment are shared among three servers (first server 500, second server 600, and third server 700). This embodiment is different from the embodiment illustrated in FIG. 21 in the point that information of control data (control command) is not included in the recipe DB 612, and the third server 700 which manages control data is additionally provided. The third server 700 includes a third database 715 including a control command DB 712 storing control data for each recipe. In this embodiment, the second server 600 additionally transmits access information for accessing the third server 700 when providing selected recipe information to a user, and the mobile terminal 300 accesses the third server 700 on the basis of this access information and obtains control data.

FIG. 24 is a flowchart illustrating a recipe information obtaining and transmitting process according to the embodiment illustrated in FIG. 23. The process illustrated in FIG. 24 is the same as the process illustrated in FIG. 22 except for the point that step S405 is executed instead of step S305 in FIG. 22, and steps S406 and S407 are added.

With the above configuration, it is possible to realize a cooker system suitable for the case in which the first server 500, which collects information necessary for providing a cloud service from the mobile terminal 300 of the user, the second server 600, which provides recipe information to the user, and the third server 700, which manages control data, are operated by different providers.

7. Configuration Example of Service Providing System

Next, a configuration example of a service providing system to which the art of the present disclosure is applicable will be described.

Figure 25A:
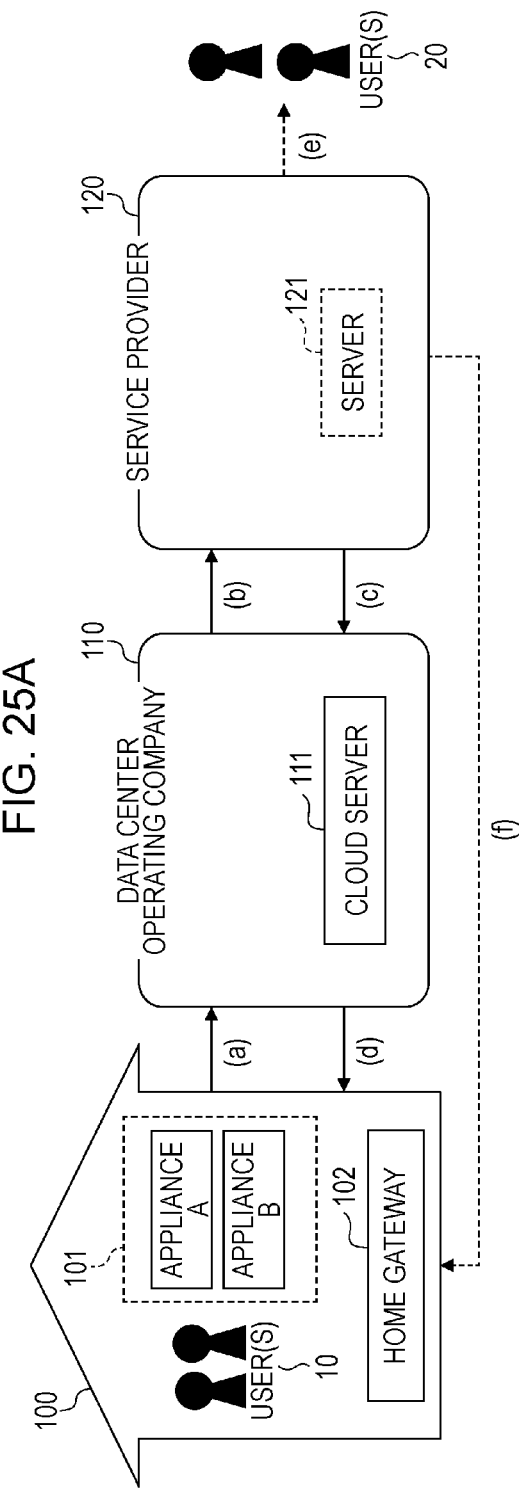
FIGS. 25A to 25C are diagrams illustrating the overall configuration of a service providing system according to the present disclosure.

FIG. 25A is a diagram illustrating the overall configuration of the service providing system. The service providing system includes a plurality of information devices located at each of a user group 100, a data center operating company 110, and a service provider 120.

The user group 100 is, for example, a company, an organization, or a family, and the size of the user group 100 does not matter. The user group 100 includes a plurality of home appliances 101 including an appliance A and an appliance B, and a home gateway 102. The plurality of home appliances 101 each have a communication function and are capable of transmitting/receiving data to/from another appliance. The plurality of home appliances 101 may include an appliance that has a configuration and a function for directly connecting to the Internet, and an appliance that does not have such a configuration or function. The former appliance may be, for example, a smartphone, a tablet terminal, a dedicated display terminal, a personal computer (PC), or a television. The latter appliance may be, for example, a cooking home appliance, a light, a washing machine, or a refrigerator. As described here, there may be an appliance connectable to the Internet via the home gateway 102. The plurality of home appliances 101 in the user group 100 are used by one or more users 10. Note that the users 10 are illustrated for the sake of description and are not included in the service providing system.

The home gateway 102 receives log information regarding the operation of each of the plurality of home appliances 101 therefrom, and transmits the log information to a cloud server 111. The home gateway 102 accumulates log information, and provides the accumulated log information to the cloud server 111 once a day, for example.

Although the single home gateway 102 is illustrated in FIG. 25A, this is only an example, and there may be a plurality of home gateways. In the case where there is a plurality of home gateways, it is only necessary that, for example, a home gateway connected to an external network (master home gateway) be connected to another home gateway (slave home gateway). The slave home gateway receives and accumulates log information from one or more of the plurality of appliances 101, and uploads the log information to a server via the master home gateway. Alternatively, the slave home gateway may output a signal for operating one or more of the plurality of appliances 101 via the master home gateway.

The data center operating company 110 includes the cloud server 111. The cloud server 111 is, for example, a virtual server that cooperates with various appliances via the Internet. The cloud server 111 manages a group of large amounts of data (so-called "big data") that are difficult to be handled with existing general technology, such as mainly a general database management tool. The data center operating company 110 performs data management, management of the cloud server 111, and operates a data center for performing such management. The details of services performed by the data center operating company 110 will be described later.

Figure 25C:
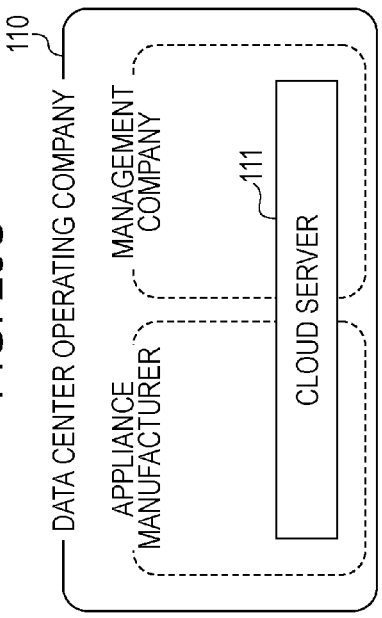
Figure 25B:
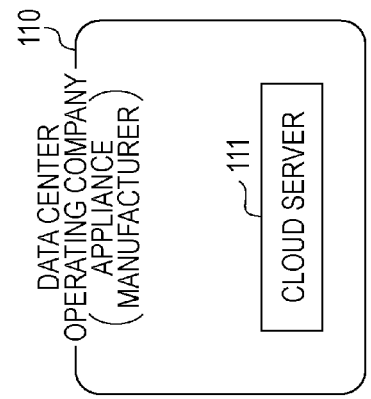

The data center operating company 110 is not limited to a company that only performs data management or only operates the cloud server 111. FIGS. 25(B) and (C) illustrate modified examples of the data center operating company 110. FIG. 25(B) illustrates an appliance manufacturer that functions as the data center operating company 110. In the case where an appliance manufacturer that develops and manufactures an appliance(s) included in the plurality of home appliances 101 additionally performs data management or manages the cloud server 111, the appliance manufacturer corresponds to the data center operating company 110. In addition, FIG. 25(C) illustrates a plurality of companies that jointly manage the single cloud server 111. As described here, the data center operating company 110 is not limited to a single company. In the case where an appliance manufacturer and another management company perform data management or operate the cloud server 111 in a joint or shared manner, both the manufacturer and the company correspond to the data center operating company 110. Although data management or management of the cloud server 111 is performed in a joint or shared manner, only one of the appliance manufacturer and the management company may function as the data center operating company 110. In addition, the data center operating company 110 may have the function of a service provider.

The above-described cloud server 111 may be realized not only as a hardware computer, but also as software in which functions necessary for the cloud server 111 are programmed.

The service provider 120 includes a server 121. The size of the "server 121" here does not matter as long as the server 121 refers to a computer or a recording medium having the function of providing data or services based on the data. For example, because of the point that data may be provided using a personal PC, the personal PC itself or, for example, a memory in the personal PC may be included in the "server 121". In addition, there is a case in which the service provider 120 does not include the server 121.

Note that the home gateway 102 is not essential in the above-described service providing system. For example, in the case where the cloud server 111 performs the entire data management, the home gateway 102 is unnecessary. In addition, in the case where all appliances at home have configurations and functions for connecting to the Internet and there is no appliance that is incapable of connecting to the Internet by itself, the home gateway 102 may be omitted. Log information may be provided directly from the plurality of home appliances 101 to the cloud server 111 via the Internet.

Next, the flow of information in the above-described service will be described.

First, the appliance A or the appliance B in the user group 100 transmits its log information to the cloud server 111 of the data center operating company 110. The cloud server 111 receives and accumulates the log information transmitted from the appliance A or the appliance B (FIG. 25(a)).

Next, the cloud server 111 of the data center operating company 110 provides the collected log information in certain units to the service provider 120. Here, the term "certain units" may be units of information accumulated by the data center operating company 110 that can be organized and provided to the service provider 120, or may be units requested by the service provider 120. Although it is described as "certain units", log information may not necessarily be provided in certain units. There may be a case in which the amount of log information to be provided changes in accordance with circumstances. Log information is saved in the server 121 included in the service provider 120 as occasion calls (FIG. 25(b)).

The service provider 120 organizes the log information as information that suits services to be provided to users, and provides the information to the users. The users to which the information is provided may be the users 10 who use or own the plurality of home appliances 101, or may be external users 20. For the method of providing services to users, for example, services may be directly provided from the service provider 120 to the users 20 (FIG. 25(e), (f)). In addition, for example, services may be provided to the users 10 again via the cloud server 111 of the data center operating company 110 (FIG. 25(c), (d)). In addition, the cloud server 111 of the data center operating company 110 may organize the log information as information that suites services to be provided to users, and provide the information to a computer of the service provider 120.

Note that the users 10 and the users 20 may be identical or different. In addition, the plurality of home appliances 101, the cloud server 111, and the server 121 need not be located in one and the same country. For example, the plurality of home appliances 101 may be located in Japan, and the cloud server 111 and the server 121 may be located in the United States, or vice versa. In the case where at least one of the cloud server 111 and the server 121 provide an analysis result or the like in response to an operation (control) by a user(s) and the user(s) can confirm the analysis result using a display terminal of a PC or the like, it can be said that the users 10 receive the benefit of the system in that country. This system is substantially the same as the case in which the plurality of home appliances 101, the cloud server 111, and the server 121 are located in one country.

If information for identifying the individual users 10 is included in log information collection (FIG. 25(*a*), (*b*)) and information provision (FIG. 25(*c*), (*d*), (*e*), (*f*)), the information may be abused. Therefore, it is possible to conceive an operation in which information for identifying the individual users 10, such as names, is not included in log information. In the case where information for identifying the individual users 10 is included, the information may be encrypted and transmitted by a transmission source in order to prevent leakage of the personal information.

8. Types of Cloud Service for Realizing Service Providing System

The art described in the above-described embodiments may be realized by the following types of cloud service, for example. Note that the types of cloud service are not limited to the following types.

8.1 Service Type 1: Self-Data-Center-Type Cloud Service

Figure 26:
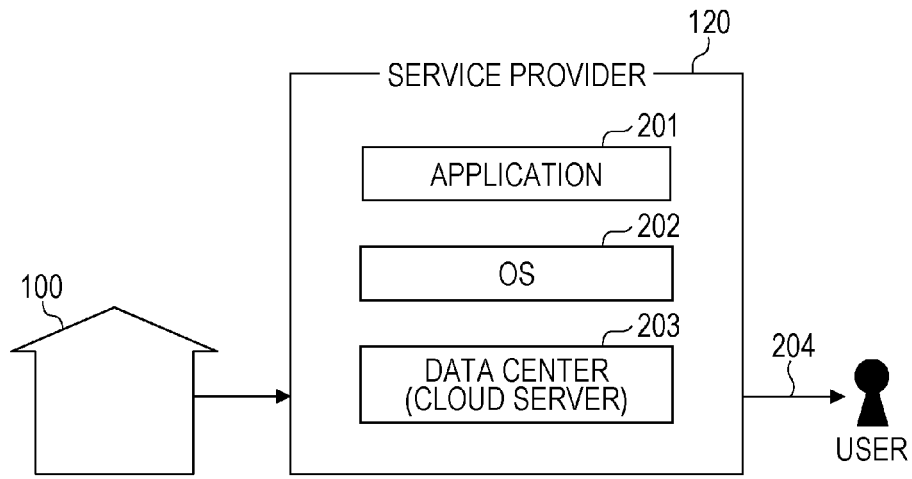
FIG. 26 is a diagram illustrating the overall configuration of a service type 1 in the service providing system according to the present disclosure.

FIG. 26 illustrates an overview of a service provided by a system using a service type 1 (self-data-center-type cloud service). In this type, the service provider 120 obtains information from the user group 100, and provides a service to a user(s). In this type, the service provider 120 has the function of a data center operating company. That is, the service provider 120 has a cloud server 203 that manages big data. Thus, there is no data center operating company.

In this type, the service provider 120 operates and manages the data center (cloud server) 203. In addition, the service provider 120 manages an operating system (OS) 202 and an application 201. The service provider 120 provides a service using the OS 202 and the application 201 managed by the service provider 120 (arrow 204).

8.2. Service Type 2: IaaS-Use Type Cloud Service

Figure 27:
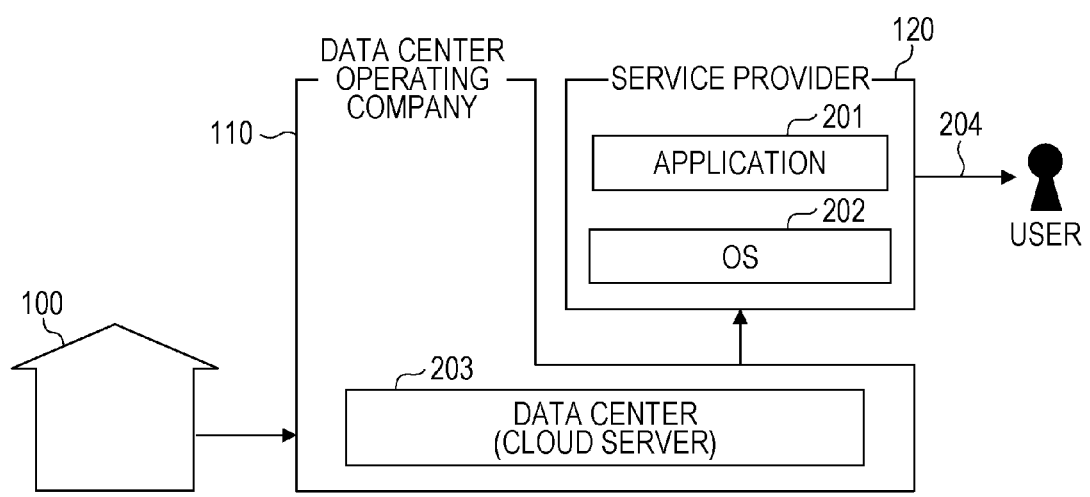
FIG. 27 is a diagram illustrating the overall configuration of a service type 2 in the service providing system according to the present disclosure.

FIG. 27 illustrates an overview of a service provided by a system according to a service type 2 (IaaS-use type cloud service). Here, "IaaS" is the acronym of "Infrastructure as a Service", and is a cloud service providing model that provides, as a service via the Internet, an infrastructure itself for constructing and running a computer system.

In this type, the data center operating company 110 operates and manages the data center (cloud server) 203. In addition, the service provider 120 manages the OS 202 and the application 201. The service provider 120 provides a service using the OS 202 and the application 201 managed by the service provider 120 (arrow 204).

8.3. Service Type 3: PaaS-Use Type Cloud Service

Figure 28:
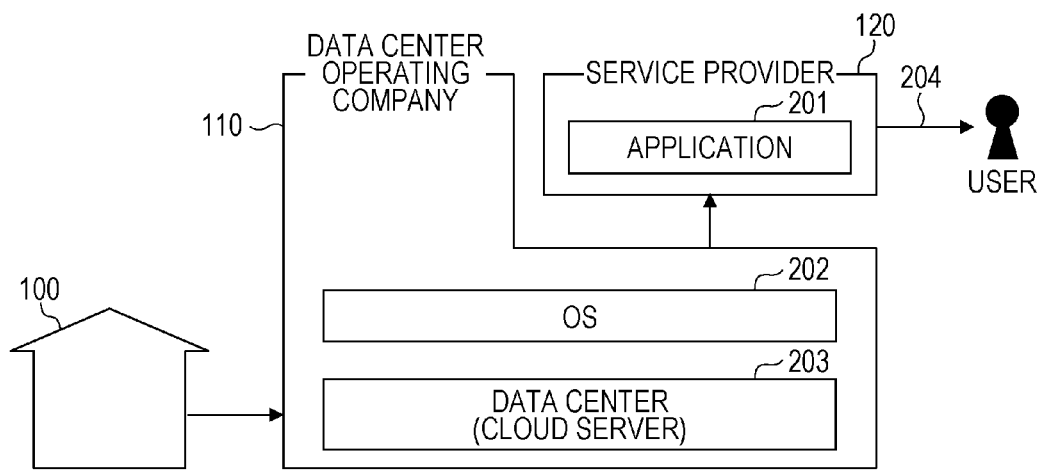
FIG. 28 is a diagram illustrating the overall configuration of a service type 3 in the service providing system according to the present disclosure.

FIG. 28 illustrates an overview of a service provided by a system according to a service system 3 (PaaS-use type cloud service). Here, "PaaS" is the acronym of "Platform as a Service", and is a cloud service providing model that provides, as a service via the Internet, a platform serving as a foundation for constructing and running software.

In this type, the data center operating company 110 manages the OS 202, and operates and manages the data center (cloud server) 203. In addition, the service provider 120 manages the application 201. The service provider 120 provides a service using the OS 202 managed by the data center operating company 110 and the application 201 managed by the service provider 120 (arrow 204).

8.4. Service Type 4: SaaS-Use Type Cloud Service

Figure 29:
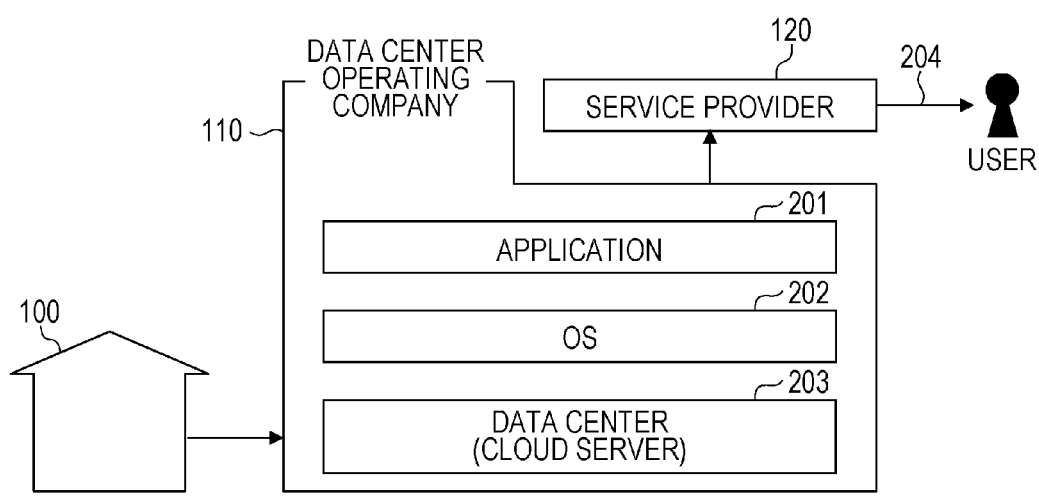
FIG. 29 is a diagram illustrating the overall configuration of a service type 4 in the service providing system according to the present disclosure.

FIG. 29 illustrates an overview of a service provided by a system according to a service system 4 (SaaS-use type cloud service). Here, "SaaS" is the acronym of "Software as a Service". The SaaS-use type cloud service is a cloud service providing model in which, for example a user such as a company or a person who does not have a data center (cloud server) has the function of using, via a network such as the Internet, an application provided by a platform provider having a data center (cloud server).

In this type, the data center operating company 110 manages the application 201, manages the OS 202, and operates and manages the data center (cloud server) 203. In addition, the service provider 120 provides a service using the OS 202 and the application 201 managed by the data center operating company 110 (arrow 204).

As described above, the service provider 120 provides a service in any of the above-described types of cloud service. In addition, for example, the service provider 120 or the data center operating company 110 may develop the OS 202, the application 201, or a database for big data by itself, or may outsource the development thereof to a third party.

The art of the present disclosure is useful in realizing a cloud service that collects and utilizes recipe information for a food item selected by a user.

What is claimed is:

1. A method for controlling an information terminal apparatus having a display, the method comprising:
    receiving, from a first server via a first network, first display data (i) causing the information terminal apparatus to indicate a condition to permit collecting selection information indicating recipe information selected by a user and (ii) asking the user for a comprehensive permission to collect the selection information under the indicated condition, recipe information (i) indicating a cooking recipe used in a cooker, and (ii) being provided by a second server, wherein certain recipe information among a plurality of items of recipe information additionally including a specific health identifier when the certain recipe information concerns a food item related to a specific constitution, disorder, disease, or allergy;
    displaying the first display data on the display;
    receiving, from the second server via a second network, (i) the selection information indicating the recipe information selected from among the plurality of items of recipe information and (ii) control data for cooking preparation in the cooker, the control data corresponding to the selected recipe information;
    displaying the selected recipe information on the display;
    transmitting the control data to the cooker for setting the cooker according to the selected recipe information; and
    determining whether the selected recipe information has the specific health identifier;

determining whether the user has granted the comprehensive permission for collecting the selection information under the indicated condition; and transmitting, to the first server for collection without asking the user for an individual permission, the selected recipe information in association with a user ID of the information terminal apparatus when the selected recipe information is determined to include the specific health identifier and it is determined that the user has granted the comprehensive permission for collecting the selection information under the indicated condition.

2. The method according to claim 1, wherein, when the selected recipe information does not have the specific health identifier, the selected recipe information, which does not have the specific health identifier, is not transmitted to the first server.

3. The method according to claim 1, wherein the first server is a server that is identical to the second server.

4. The method according to claim 1, wherein the first server is a server that is different from the second server.

5. The method according to claim 1, wherein the determining of whether or not the selected recipe information has the specific health identifier is performed when transmitting the control data to the cooker.

6. The method according to claim 5, further comprising after receiving a response from the cooker indicating that the setting is completed, transmitting the selected recipe information to the first server.

7. The method according to claim 1, further comprising after transmitting the selected recipe information having the specific health identifier to the first server, causing the selected recipe information to be in a state in which the selected recipe information is set to be deleted from the information terminal apparatus when a predetermined condition occurs.

8. The method according to claim 1, further comprising after transmitting the selected recipe information having the specific health identifier to the first server, displaying, on the display, second display data indicating that the selected recipe information having the specific health identifier has been transmitted to the first server.

9. The method according to claim 1, wherein the first display data includes an item for specifying a period for the granted comprehensive permission.

10. The method according to claim 1, wherein the cooker is a microwave oven.

11. A computer-readable non-transitory recording medium storing a program used in an information terminal apparatus having a display, the program causing the information terminal apparatus to:

receive, from a first server via a first network, first display data (i) causing the information terminal apparatus to indicate a condition to permit collecting selection information indicating recipe information selected by a user and (ii) asking the user for a comprehensive permission to collect the selection information under the indicated condition, recipe information (i) indicating a cooking recipe used in a cooker, and (ii) being provided by a second server, wherein certain recipe information among a plurality of items of recipe information additionally including a specific health identifier when the certain recipe information concerns a food item related to a specific constitution, disorder, disease, or allergy;

display the first display data on the display;

receive, from the second server via a second network, (i) the selection information indicating the recipe information selected from among the plurality of items of recipe information and (ii) control data for cooking preparation in the cooker, the control data corresponding to the selected recipe information;

display the selected recipe information on the display;

transmit the control data to the cooker for setting the cooker according to the selected recipe information; and determine whether the selected recipe information has the specific health identifier;

determine whether the user has granted the comprehensive permission for collecting the selection information under the indicated condition; and transmit, to the first server for collection without asking the user for an individual permission, the selected recipe information in association with a user ID of the information terminal apparatus when the selected recipe information is determined to include the specific health identifier and it is determined that the user has granted the comprehensive permission for collecting the selection information under the indicated condition.

12. A cooker system comprising:

a cooker;

a first server that collects information;

a second server that provides recipe information indicating a cooking recipe used in the cooker; and an information terminal apparatus having a display, the information terminal apparatus configured to control the cooker, wherein the first server transmits, via a first network to the information terminal apparatus, first display data (i) causing the information terminal apparatus to indicate a condition to permit collecting selection information indicating recipe information selected by a user and (ii) asking the user for a comprehensive permission to collect the selection information under the indicated condition, recipe information (i) indicating a cooking recipe used in the cooker, and (ii) being provided by a second server, wherein certain recipe information among a plurality of items of recipe information additionally including a specific health identifier when the certain recipe information concerns a food item related to a specific constitution, disorder, disease, or allergy, wherein the first display data is displayed on the display, wherein the second server transmits, via a second network to the information terminal apparatus, (i) the selection information indicating the recipe information selected from among the plurality of items of recipe information and (ii) control data for cooking preparation in the cooker, the control data corresponding to the selected recipe information, wherein the information terminal apparatus displays the selected recipe information on the display, wherein the information terminal apparatus transmits the control data to the cooker for setting the cooker according to the selected recipe information, wherein the information terminal apparatus determines whether the selected recipe information has the specific health identifier, wherein the information terminal apparatus determines whether the user has granted the comprehensive permission for collecting the selection information under the indicated condition, and wherein, the information terminal apparatus transmits to the first server for collection without asking the user for an individual permission, the selected recipe information in association with a user ID of the information terminal apparatus when the selected recipe information is determined to include the specific health identifier and it is determined that the user has granted the comprehensive permission for collecting the selection information under the indicated condition.

13. A cooker used in the cooker system according to claim 12.

14. A cooker in a cooker system including a first server that collects information, a second server that provides recipe information, the recipe information indicating a cooking recipe used in the cooker, wherein certain recipe information among a plurality of items of recipe information additionally includes a specific health identifier when the certain recipe information concerns a food item related to a specific constitution, disorder, disease, or allergy, an information terminal apparatus having a display that connects to the first server and receives first display data (i) causing the information terminal apparatus to indicate a condition to permit collecting selection information indicating recipe information selected by a user and (ii) asking the user for a comprehensive permission to collect the selection information under the indicated condition, and the information terminal apparatus that connects to the second server and receives (i) the selection information indicating the recipe information selected from among the plurality of items of recipe information and (ii) control data for cooking preparation in the cooker, the control data corresponding to the selected recipe information, and the cooker configured to be controlled by the information terminal apparatus, the cooker comprising:
 a receiver that receives the control data, from the information terminal apparatus, for setting the cooker according to the selected recipe information;
 a controller that sets the cooker according to the control data; and
 a heating unit controlled by the controller based on the set control data,
 and
 wherein the selected recipe information is determined to include the specific health identifier and determined that the user has granted the comprehensive permission for collecting the selection information under the indicated condition, without asking the user for an individual permission.

15. A method for controlling an information terminal apparatus configured to connect to a first server that collects information, to a second server that provides recipe information indicating a cooking recipe used in a cooker, and to a third server that manages control data used in the cooker for a cooking preparation corresponding to the recipe information, the method comprising:
 receiving, from the first server via a first network, first display data (i) causing the information terminal apparatus to indicate a condition to permit collecting selection information indicating the recipe information selected by a user and (ii) asking the user for a comprehensive permission to collect the selection information under the indicated condition, recipe information indicating a cooking recipe used in a cooker, wherein certain recipe information among a plurality of items of recipe information additionally including a specific health identifier when the certain recipe information concerns a food item related to a specific constitution, disorder, disease, or allergy;
 displaying the first display data on a display;
 receiving, from the second server via a second network, (i) the selection information indicating the recipe information selected from among the plurality of items of recipe information and (ii) access information for accessing the third server to obtain control data corresponding to the selected recipe information;
 displaying the selected recipe information on the display;
 accessing, based on the access information, the third server via a third network, and receiving the control data corresponding to the selected recipe information;
 transmitting the received control data to the cooker for setting the cooker according to the selected recipe information;
 determining whether the selected recipe information has the specific health identifier;
 determining whether the user has granted the comprehensive permission for collecting the selection information under the indicated condition; and
 transmitting, to the first server for collection without asking the user for an individual permission, the selected recipe information in association with a user ID of the information terminal apparatus when the selected recipe information is determined to include the specific health identifier and it is determined that the user has granted the comprehensive permission for collecting the selection information under the indicated condition.

16. A computer-readable non-transitory recording medium storing a program used in an information terminal apparatus configured to connect to a first server that collects information, to a second server that provides recipe information indicating a cooking recipe used in a cooker, and to a third server that manages control data used in the cooker for a cooking preparation corresponding to the recipe information, the program causing the information terminal apparatus to:
 receive, from the first server via a first network, first display data for causing the information terminal apparatus to indicate a condition to permit collecting selection information indicating recipe information and for asking the user for a comprehensive permission to collect the selection information under the indicated condition, recipe information (i) indicating a cooking recipe used in a cooker, and (ii) being provided by a second server, wherein certain recipe information among a plurality of items of recipe information additionally including a specific health identifier when the certain recipe information concerns a food item related to a specific constitution, disorder, disease, or allergy;
 display the first display data on a display;
 receive, from the second server via a second network, (i) the selection information indicating the recipe information selected from among the plurality of items of recipe information and (ii) access information for accessing the third server to obtain control data corresponding to the selected recipe information;
 display the selected recipe information on the display;
 access, based on the access information, the third server via a third network, and receiving the control data corresponding to the selected recipe information;
 transmit the received control data to the cooker for setting the cooker according to the selected recipe information;
 determining whether the selected recipe information has the specific health identifier;
 determining whether the user has granted the comprehensive permission for collecting the selection information under the indicated condition; and
 transmit, to the first server for collection without asking the user for an individual permission, the selected recipe information in association with a user ID of the information terminal apparatus when the selected recipe information is determined to include the specific health identifier and it is determined that the user has granted the comprehensive permission for collecting the selection information under the indicated condition.

* * * * *